United States Patent [19]

Masuya et al.

[11] Patent Number: 5,344,928
[45] Date of Patent: Sep. 6, 1994

[54] PHENOTHIAZINE DERIVATIVES, THEIR PRODUCTION AND USE

[75] Inventors: Hirotomo Masuya, Kawabe; Hiroshi Shimadzu, Settsu; Toshio Miyawaki, Nishinomiya; Marvin A. Motsenbocker, Amagasaki, all of Japan

[73] Assignee: Takeda Chemical Industries, Ltd., Osaka, Japan

[21] Appl. No.: 868,100

[22] Filed: Apr. 14, 1992

[30] Foreign Application Priority Data

Apr. 26, 1991 [JP] Japan .................................. 3-096930

[51] Int. Cl.⁵ .............................................. C07D 279/28
[52] U.S. Cl. ......................................................... 544/37
[58] Field of Search ....................................... 544/37, 32

[56] References Cited

U.S. PATENT DOCUMENTS

| | | | |
|---|---|---|---|
| 3,873,340 | 3/1975 | Miyazawa et al. | 544/37 |
| 4,394,443 | 7/1983 | Weissman et al. | 435/6 |
| 4,548,904 | 10/1985 | Kent et al. | 436/89 |
| 4,652,643 | 3/1987 | Gunn et al. | 544/37 |
| 4,714,763 | 12/1987 | Theodoropulos | 544/31 |
| 4,962,197 | 10/1990 | Foley et al. | 544/31 |

FOREIGN PATENT DOCUMENTS

| | | |
|---|---|---|
| 3305304 | 8/1984 | Fed. Rep. of Germany . |
| 63-12278 | 1/1988 | Japan . |
| 872683 | 7/1961 | United Kingdom . |

OTHER PUBLICATIONS

Inoue et al., "Cloning and Sequencing of the Gene Encoding . . . " J. of Bacteriology 171: 3115–3122 (Jun. 1989).

Nunn et al., "Isolation and Complementation of 10 Methanol . . . " J. of Bacteriology 166: 581–597 (May 1986).

*Primary Examiner*—Mukund J. Shah
*Assistant Examiner*—P. K. Sripada
*Attorney, Agent, or Firm*—Wegner, Cantor, Mueller & Player

[57] ABSTRACT

There is disclosed a novel phenothiazine derivative of the general formula (I):

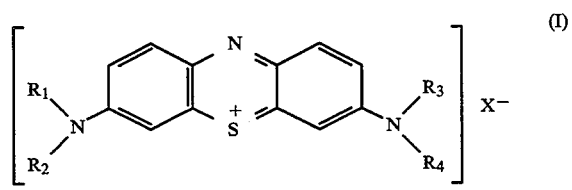

wherein $R_1$, $R_2$, $R_3$ and $R_4$ are the same or different and are a $C_{1-6}$ alkyl group and at least one of them has as a substituent a group which can react with amino group, thiol group or carboxyl group, and $X^-$ is a counter ion of the phenazathionium. Their production and the intermediates used in the production are also disclosed. The compound (I) is a derivative of methylene blue and is applicable to photodynamic therapy of cancer or immunoassays utilizing chemiluminescence.

10 Claims, 2 Drawing Sheets

PHENOTHIAZINE DERIVATIVES, THEIR PRODUCTION AND USE

FIELD OF THE INVENTION

The present invention relates to novel phenothiazine derivatives, their production and use. The compounds of the present invention are derivatives of methylene blue, which is one of the photosensitive dyes, and are capable of binding to antibody proteins and the like. The compounds of the present invention are expected to be applicable to photodynamic therapy of cancer or immunoassays utilizing chemiluminescence.

BACKGROUND OF THE INVENTION

As practical examples utilizing an oxidative characteristic reaction of photosensitive dyes, disinfection and sterilization of service water with methylene blue are well known.

Various studies have been hitherto done on light excitation activities of photosensitive dyes such as xanthines (e.g., rose bengal, fluorescein, eosin, erythrosine, etc.), phenothiazines (the representative example of which is methylene blue), porphyrins and the like. And, there is a tendency to increase in the use of photosensitive dyes in the fields of clinical drugs or diagnostics of cancer.

Among these photosensitive dyes, methylene blue has extremely strong photo-oxidation activity and is advantageous in that it absorbs light of long wavelength (670 nm) which is readily passed through a living body tissue. As reported by Foote in "Mechanisms of Photosensitized Oxidation", Jan. 29, 1968, Vol. 162, pp. 963–970, it is considered that the activities due to excitation of methylene blue by light mainly result from two reactions. That is, it is considered that, in the case of Type I light excitation reaction, an excited dye directly reacts with a substrate and that, in the case of Type II light excitation reaction, firstly, an excited triplet dye reacts with molecular oxygen to produce singlet oxygen, and then a substrate is oxidized with the singlet oxygen. Which type of the reaction occurs depends on concentrations of particular dye, dissolved oxygen and substrate to be used.

Recently, among these photosensitive dyes, in particular, the use of porphyrins in treatment of cancer has been reported (Analytical Chemistry, Vol. 61, Dec. 15, 1989, pp. 1367–1375). According to this report, a porphyrin is injected into a cancer tissue or in the vicinity thereof and light energy is provided from outside of the body to excite the porphyrins. Singlet oxygen is produced which causes a lethal effect on cancer cells. One of the important characteristics of these dyes is that the dyes can absorb light of long wavelength ($>$650 nm) which can be passed through a living body tissue.

Recently, as an attempt at such a cancer treatment, an improved technique has been reported in which specificity in an antigen-antibody reaction is utilized. That is, in this technique, a photosensitive porphyrin dye is bound to an antibody against cancer, whereby the cancer cells per se, which are the antigen, are attacked specifically (JO 2059-585-A, EP 252683). However, it is not easy to bind most of these photosensitive dyes to an antibody protein.

Thus, if a highly reactive photosensitive dye is readily available which is easy to bind to proteins and is capable of absorbing light of long wavelength ($>$650 nm), significant improvements are expected in this art.

Another important use of photosensitive dyes is that in the field of diagnostics. For example, the photosensitive dye as described herein can be used for labeling an antibody, hapten or nucleic acid (DNA or RNA) probe. The labeled antibody, hapten or nucleic acid probe thus obtained is used to produce a signal indicating the original amount of an analyte in the course of a clinical chemical analysis. The signal is derived from the labeled photosensitive dye and a representative example thereof is color development, fluorescence or chemiluminescence. However, this technique has scarcely been employed because it is difficult to obtain a highly reactive derivative of photosensitive dye which is capable of covalently binding to a protein, hapten or nucleic acid.

The desired derivative of a photosensitive dye is that having an active functional group which can readily react with a protein, hapten or nucleic acid under normal reaction conditions. One of these active functional groups is a succinimido ester group which can react with an amino group of proteins or nucleic acids. Another group is a maleimide group which can react with a thiol group of proteins. However, it is difficult to introduce these functional groups directly into methylene blue dye. This is clear from the fact that no methylene blue derivative capable of modifying proteins or nucleic acids has yet found, even though methylene blue has been studied for more than 50 years.

When an aromatic compound having low molecular weight such as a dye is bound to a protein, hapten (e.g., thyroid hormone) or nucleic acid, problems often arise such as sedimentation of a protein-dye conjugate and non-specific binding of the protein, hapten or nucleic acid to the surface of a solid phase. These problems are caused by the hydrophobic nature of the dye in an aqueous solution, which results in a low solubility of the protein-dye conjugate and non-specific absorption of the protein, hapten or nucleic acid to the surface of the solid phase. Thus, if any technique could improve such an instability of a protein-dye conjugate or prevent such non-specific adsorption, it would be possible to improve conventional techniques to a great extent.

OBJECTS OF THE INVENTION

Under these circumstances, the present inventors have synthesized and studied various reactive derivatives of methylene blue. As a result, it has been found that introduction of a hydrophilic group such as a carboxyl group or the like into the methylene blue skeleton is effective for improving instability of a protein-dye conjugate. Thus, the present invention has been completed.

An object of the present invention is to provide a novel photosensitive dye derivative which is capable of modifying antibody proteins and the like.

Another object of the present invention is to provide an immunoassay method using the novel photosensitive dye derivative.

These objects as well as other objects and advantages of the present invention will become apparent to those skilled in the art from the following description with reference to the accompanying drawings.

SUMMARY OF THE INVENTION

Figure 1:
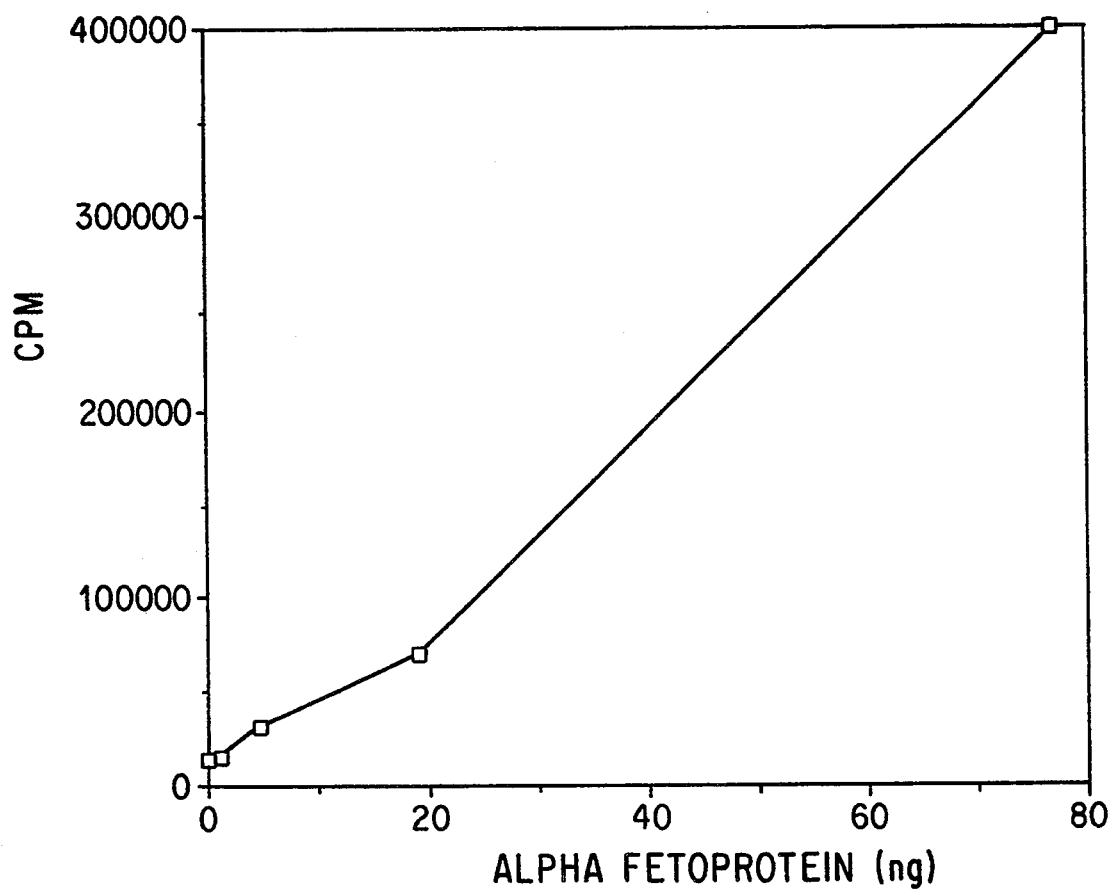
FIG. 1 illustrates the result of alpha fetoprotein assay obtained in Example 15 described hereinafter.

According to the present invention, there are provided:

(1) A phenothiazine derivative of the general formula (I):

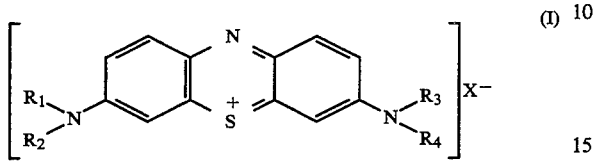

wherein $R_1$, $R_2$, $R_3$ and $R_4$ are the same or different and are respectively a $C_{1-6}$ alkyl group, at least one of which has as a substituent a group which can react with amino group, thiol group or carboxyl group, and $X^-$ is a counter ion of the phenazathionium;

(2) A phenothiazine derivative of the general formula (II):

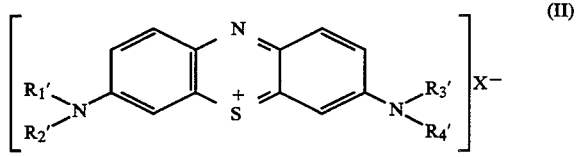

wherein at least one of $R_1'$, $R_2'$, $R_3'$ and $R_4'$ is a group of the formula: $-(CH_2)_m-CO-Y$, the others are $C_{1-6}$ alkyl group, Y is a leaving group, m is an integer of 1 to 6 and $X^-$ is a counter ion of the phenazathionium;

(3) An indaminethiosulfonic acid derivative of the general formula (III):

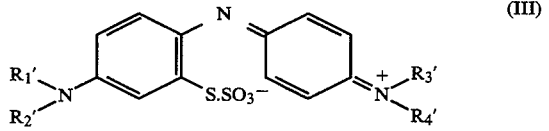

wherein $R_1'$, $R_2'$, $R_3'$ and $R_4'$ are as defined above;

(4) A 2-amino-5-disubstituted aminophenyl thiosulfonic acid derivative of the general formula (IV):

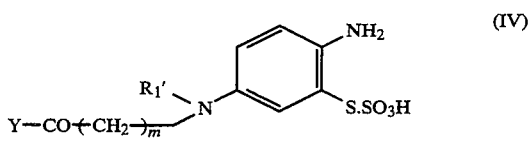

wherein Y and m are as defined above, and $R_1''$ is a $C_{1-6}$ alkyl group;

(5) An indaminethiosulfonic acid derivative of the general formula (V):

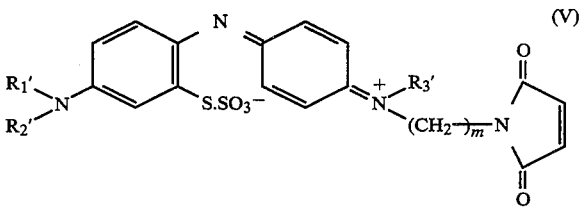

wherein $R_1'$, $R_2'$ and $R_3'$ are as defined above;

(6) A process for producing the phenothiazine derivative of the general formula (I), which comprises the steps of:
removing the group Y of the phenothiazine derivative of the general formula (II), and
introducing a group which can react with amino group, thiol group or carboxyl group;

(7) A process for producing the phenothiazine derivative of the general formula (I), which comprises the steps of:
subjecting the indaminethiosulfonic acid derivative of the general formula (III) to oxidative ring closure with an inorganic oxidizing agent in water, an organic solvent or a mixed solvent thereof to obtain the phenothiazine derivative of the general formula (II),
removing the group Y, and
introducing a group which can react with amino group, thiol group or carboxyl group;

(8) A process for producing a compound of the general formula (VII):

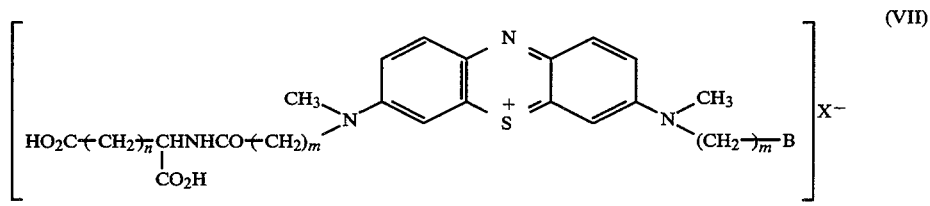

wherein B is succinimidoxycarbonyl group or maleimido group, m is an integer of 1 to 6 and n is 1 or 2, which comprises the steps of:
reacting a succinimido ester derivative of the general formula (VI):

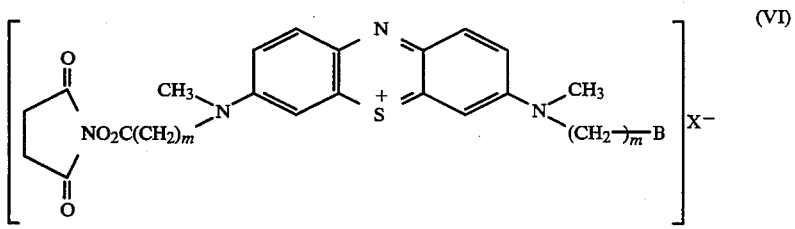

wherein B and m are as defined above, with a triethylamine salt of an acidic amino acid;

(9) A method for the determination of an analyte in a sample comprising measuring a conjugate formed by coupling the phenothiazine derivative of the general formula (I) to an antigen or antibody; and

(10) A labeled conjugate of an antigen or antibody comprising the phenothiazine derivative of the general formula (I) coupled to the antigen or antibody through amino group, thiol group or carboxyl group of the latter.

DETAILED EXPLANATION OF THE INVENTION

In $R_1$ to $R_4$ of the compound of the above general formula (I), the group which can react with amino group, thiol group or carboxyl group is not specifically limited. The group may be any one which can react with analytes in immunoassays and the like, such as proteins, haptens, peptides, nucleic acids, amino acids and the like. Examples of the group which can react with amino group include carboxyl group, halogenocarbonyl groups (e.g., chlorocarbonyl group, etc.), azidocarbonyl group, cyanocarbonyl group, alkoxycarbonyloxycarbonyl groups (e.g., ethoxycarbonyloxycarbonyl group, isobutoxycarbonyloxycarbonyl group, etc.), substituted phenoxycarbonyl groups (e.g., p-nitrophenoxycarbonyl group, 2,4-dinitrophenoxycarbonyl group, pentachlorophenoxycarbonyl group, 2,4,5-trichlorophenoxycarbonyl group, pentafluorophenoxycarbonyl group, etc.), 1-imidazolylcarbonyl group, 1-benzotriazolyloxycarbonyl group, 5-norbornene-2,3-dicarboximidoxycarbonyl group, succinimidoxycarbonyl group, maleimidoxycarbonyl group, aspartic acid residue, glutamic acid residue and the like. Examples of the group which can react with thiol group include maleimido group and the like. Examples of the group which can react with carboxyl group include an aminoalkylcarbamoyl groups (e.g., aminoethylcarbamoyl group, aminodecylcarbamoyl group, etc.) and the like. In view of the object of the present invention, at least one of $R_1$ to $R_4$ groups should be such a reactive group. Further, in view of the object of the present invention, the compound of the general formula (I) is preferably hydrophilic. The number of such a reactive group is suitably selected, taking into account the combination with the other groups of $R_1$ to $R_4$. The $C_{1-6}$ alkyl group represented by $R_1$, $R_2$, $R_3$ and $R_4$ respectively may be the same or different and are a straight or branched chain $C_{1-6}$ alkyl group such as methyl, ethyl, propyl, isopropyl, butyl, sec-butyl, tert-butyl, pentyl, isopentyl, neopentyl, hexyl, isohexyl or the like. In view of the structural similarity to methylene blue and hydrophilic nature, methyl and ethyl are especially preferred. The $C_{1-6}$ alkyl group of $R_1'$ to $R_4'$ and the other groups included in the present specification is as defined above.

As the group represented by X in the above general formulas (I) and (II) which can form a counter ion of the phenazathionium, there are mentioned halogens (e.g., chlorine, bromine, iodine, fluorine), hydroxyl, perchloric acid, sulfuric acid, nitric acid, trifluoroacetic acid, hydrofluoroboric acid and the like.

The leaving group represented by Y of the group —$(CH_2)_m$—CO—Y in the above general formulas (II), (III), (IV) and (V) may be a conventional leaving group used in the field of peptide synthesis, B-lactam antibiotic synthesis or the like. Examples thereof include lower alkoxy groups having 1 to 4 carbon atoms such as methoxy, ethoxy, propoxy, sec-butoxy, tert-butoxy and the like; aralkyloxy groups such as benzyloxy, p-nitrobenzyloxy, p-methylthiobenzyloxy, diphenylmethoyloxy, 4-pyridylmethoxy and the like; and 1-phenoxy-ethoxy group and the like.

The compound of the general formula (I) can be obtained, for example, by removing Y of the phenothiazine derivative of the general formula (II) and then introducing the group which can react with amino group, thiol group or carboxyl group. For example, it can be produced according to the process illustrated in Chart 1.

Chart 1

In Chart 1, m is an integer of 1 to 6, n is 1 or 2 and $X^-$ is a counter ion of the phenazathionium.

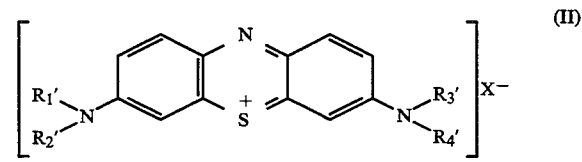

wherein at least one of $R_1'$, $R_2'$, $R_3'$ and $R_4'$ is —$(CH_2)_m$—CO—Y, Y is a leaving group and the other groups are a $C_{1-6}$ alkyl group.

hydrolysis,
catalytic reduction,
acidolysis, etc.

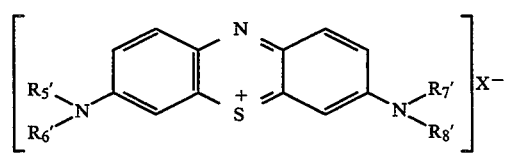

wherein at least one of $R_5'$, $R_6'$, $R_7'$ and $R_8'$ is —$(CH_2)_m$—$CO_2H$ and the other groups are a $C_{1-6}$ alkyl group.

formation of activated ester,
halide, azide, mixed acid
anhydride, etc.

↓

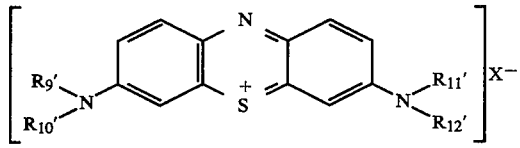

wherein at least one of $R_9'$, $R_{10}'$, $R_{11}'$ and $R_{12}'$ is —$(CH_2)_m$—COA (wherein —COA is a group which can react with amino group) and the other groups are a $C_{1-6}$ alkyl group.

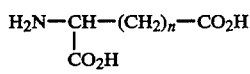

↓

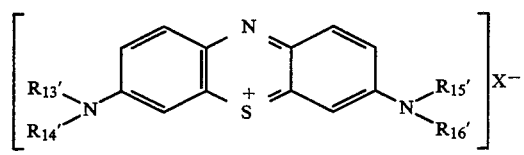

wherein at least one of $R_{13}'$, $R_{14}'$, $R_{15}'$ and $R_{16}'$ is

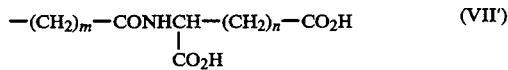     (VII')

and the other groups are a $C_{1-6}$ alkyl group or —$(CH_2)_m$—COA (wherein —COA is as defined above).

That is, (1) Among the phenothiazine derivatives of the general formula (I), the compound wherein at least one of $R_1$ to $R_4$ is a group which can react with amino group can be obtained according to a known method by subjecting the compound of the general formula (II) to hydrolysis, catalytic reduction or acidolysis and then converting the resulting carboxylic acid derivative into its halide, azide, mixed acid anhydride or activated ester.

Examples of the group represented by —COA in the Chart 1 which can react with amino group include the groups include those described with respect to the above $R_1$ to $R_4$ other than aspartic acid residue and glutamic acid residue.

Normally, hydrolysis of the ester of the formula (II) can be carried out in a 1N solution of a mineral acid or caustic alkali at a reaction temperature of 20° to 30° C. The reaction time required is normally 20 minutes to 48 hours. In general, however, the yield is low under these conditions because degradation of the phenothiazine skeleton proceeds simultaneously. This tendency is especially pronounced under alkaline conditions. When the leaving group in the compound (II) is an aralkyloxy group such as benzyloxy, p-nitrobenzyloxy, 4-pyridylmethoxy, diphenylmethyloxy or the like, it can be removed by catalytic reduction. Normally, the reaction is carried out by treatment with a palladium catalyst in an inert solvent at ordinary temperature and pressure in a stream of hydrogen. Although, when the ester group is removed, the phenothiazine skeleton is also reduced to form a phenothiazine derivative in the form of leuco, it is oxidized with air rapidly to the original phenothiazine. On the other hand, an alkoxy group such as tert-butoxy, an aralkyloxy group such as p-methylthiobenzyloxy, diphenylmethyloxy or the like, or 1-phenoxyethoxy group can be removed readily by treatment in formic acid or trifluoroacetic acid. Normally, the reaction is completed in 30 to 60 minutes at a reaction temperature of 0° to 25° C. The organic acid can be used alone or as a mixture with an inert solvent. Among the leaving groups in the general formula (II), in view of the ease of the removal and purification after the removal, the tert-butoxy group is the most preferred. That is, when the leaving group is the tert-butoxy group, the product can be used in the next step merely by concentrating it to dryness after completion of the reaction. If further purification is required, the product can be subjected to silica gel column chromatography (eluent: $MeCN/H_2O/1N$ HCl=40:5:1).

The carboxylic acid derivative thus obtained can be converted into a reactive derivative such as an acid chloride, an acid azide, a mixed acid anhydride or an activated ester or the like in order to couple the carboxylic acid derivative with a compound having an amino group.

This step is further illustrated in detail below.

Acid Chloride Method

The carboxylic acid derivative is reacted with a chloride such as thionyl chloride, oxalyl chloride, trichloromethylchloroformate (diphosgene), bistrichloromethylcarbonate (triphosgene) or the like in an inert solvent such as dichloromethane, chloroform, carbon tetrachloride, benzene or the like at 0° to 25° C. to obtain the corresponding acid chloride. Then the acid chloride is subjected to coupling with an amino compound in the presence of an organic tertiary amine such as triethylamine, diisopropylethylamine, pyridine, 4-dimethylaminopyridine or the like.

Acid Azide Method

A hydrazide derivative derived from the carboxylic acid derivative is reacted with sodium nitrite in an acidic solution according to the method of Curtius [Chem. Ber., 35, 3226 (1902)]. The reaction mixture is neutralized. Then the resulting acid azide is extracted with a solvent and subjected to the coupling, or the neutralized reaction mixture can be subjected to the coupling in situ. Alternatively, this azidation can be in a non-aqueous solvent by using an alkyl nitrite instead of sodium nitrite [J. Rudinger, et al., Collect. Czech. Chem. Commun., 26., 2333 (1961)]. Further, this derivative can also be synthesized by using diphenylphosphoryl azide (DPPA) [T. Shioiri et al., J. Am. Chem. Soc., 94, 6203 (1972)].

Mixed Acid Anhydride Method

As an acid component which forms a mixed acid anhydride with a carboxylic acid derivative, a monoalkyl carbonate is preferred. The mixed acid anhydride can be obtained by reacting a carboxylic acid derivative with ethoxycarbonyl chloride [T. Wieland et al., Ann. Chem., 572, 190 (1951); R. A. Boissonnas, Helv. Chim. Acta., 34, 874 (1951)]or isobutoxycarbonyl chloride [J. R. Vaughan et al., J. Am. Chem. Soc., 74, 676 (1952)]in the presence of an organic tertiary amine at −15° to −5° C. The mixed acid anhydride can react directly with an amino compound.

Activated Ester Method

A phenyl ester having an electron-withdrawing substituent is known as one of the activated esters used in peptide synthesis and is also applicable to the carboxylic acid derivative in the present invention. That is, esters formed with p-nitrophenol, 2,4-dinitrophenol, pentachlorophenol, 2,4,5-trichlorophenol, pentafluorophenol and the like are preferred. On the other hand, O-acylhydroxylamine esters are known as the other important activated ester. Examples thereof include ester derivatives of 1-hydroxybenzotriazole [W. Koenig et al., Chem. Ber., 103, 788 (1970)], N-hydroxysuccinimide [G. W. Anderson et al., J. Am. Chem. Soc., 85, 3039 (1963); ibid. 86, 1839 (1964)], N-hydroxymaleimide (which can be produced according to the same manner as that of N-hydroxysuccinimide) or N-hydroxy-5-norbornene-2,3-dicarboximide [M. Fujino et al., Chem. Pharm. Bull., 22, 1857 (1974)]and the like. Further, esters formed with N-hydroxyphthalimide [G. H. L. Nefkeus et al., J. Am. Chem. Soc., 83, 1263 (1961)]can be used according to the same manner. These activated ester derivatives can be obtained by reacting a mixture of both reactants with a condensing agent such as N,N-dicyclohexylcarbodiimide (DCC) or 1-ethyl-3-(3dimethylaminopropyl)carbodiimide hydrochloride (WSC: water soluble carbodiimide) or the like.

In addition to the above methods, the reactive derivatives can be obtained as follows. 1-Acylimidazole can be obtained by the reaction with 1,1'-carbonyldiimidazole (CDI) [S. Staab, Angew. Chem. Internat. Edit., 1, 351 (1962)]. Acylcyanide can be obtained by the reaction with diethylphosphoric acid cyanide (DEPC) [T. Shioiri et al., Tetrahedron Lett., 1973, 1595]. Any reactive derivative can be used directly for the reaction with an amino derivative.

Among the phenothiazine derivatives of the general formula (I) thus obtained, the compounds wherein at least one of $R_1$ to $R_4$ is a group which can react with amino group, can form peptide bond with amino compounds such as proteins, haptens, nucleic acids, amino acids and the like by selecting the above appropriate coupling method. The condensation method is not specifically limited and can be selected appropriately depending the upon nature of a particular amino compound.

In particular, as the coupling method which can also be used in a water-containing solvent, the azide method, the mixed acid anhydride method or the activated ester method is preferred. In view of stability, high reactivity of the reactive derivative and facility in purification after completion of the reaction, esters of O-acylhydroxylamines, especially, N-hydroxysuccinimide are most preferred.

The succinimido ester can be produced, for example, as follows. The monoester can be obtained by reacting the equivalent amount of dicyclohexylcarbodiimide (DCC) or 1-ethyl-3-(3-dimethylaminopropyl)carbodiimide hydrochloride (WSC) at 20° to 40° C. for 1 to 48 hours in the presence of N-hydroxysuccinimide (2 to 3 equivalents) in an anhydrous aprotic solvent such as acetonitrile, dimethylacetamide or dimethylformamide. In the case of a dicarboxylic acid, a mixture containing the monoester and diester the major portion of which is the monoester is obtained. In order to obtain the diester, it is preferred to use the reagent in an amount of 3 to 6 equivalents.

In these esterification, especially succinimide esterification, it is preferred to use an activated ester of N-hydroxysuccinimide such as N,N'-disuccinimidocarbonate (DSC) (H. Ogura et al., Tetrahedron Lett., 1979, 4745) or N,N'-disuccinimidooxalate (DSO) [H. Ogura, Tetrahedron Lett., 24, 4451 (1983)]. Normally, it is preferred to use the above activated ester in an amount of 1.5 to 3 equivalents in the case of the monoesterification or 3 to 6 equivalents in the case of the diesterification in an inert solvent such as acetonitrile, tetrahydrofuran, dioxane, acetone or the like in the presence of an organic base such as pyridine, triethylamine or the like in an amount of 2 equivalents based on the activated ester.

Normally, the reaction is completed in 1 to 3 hours at 20 to 30° C. When the starting material is a dicarboxylic acid derivative, it is often difficult to produce the monoester only. These two esters can be separated by column chromatography using Sephadex® LH-20 (eluent: acetonitrile). The succinimido ester thus obtained is reacted with triethylamine salt of aspartic acid or glutamic acid in MeCN/H$_2$O (3:1) at 25° C. for 10 minutes to obtain the compound of the general formula (VII) or the general formula (VII') in the Chart 1.

(2) Among the phenothiazine derivatives of the general formula (I), the compound wherein at least one of $R_1$ to $R_4$ is a group which can react with thiol group, namely a maleimido group, for example, the compound having a maleimidoalkyl group as $R_4$ (the compound of the general formula (VI) and (VII) wherein B is a maleimido group) can be obtained by treating the compound of the general formula (II) wherein $R_4'$ is a maleimidoalkyl group obtained from the general formula (V) (i.e., the compound of the general formula (III) wherein $R_4'$ is a maleimidoalkyl group) according to the same manner as that of the compound having a group which can react with amino group.

(3) Among the compounds of the general formula (I), the phenothiazine derivative wherein at least one of $R_1$ to $R_4$ is a group which can react with carboxyl group can be obtained by reacting the reactive derivative of phenothiazine carboxylic acid described (I) above with a diamino compound of the formula H$_2$N—(CH$_2$-)$_p$—NH$_2$ (wherein p is an integer of 2 to 10). The monoacylaminoalkylamine thus obtained is further reacted with another carboxyl group or its reactive derivative.

The compound of the general formula (II) which is the starting material for the production of the compound of the general formula (I) can also be obtained by the process as shown in the Chart 2 according to a per se known synthesis method of methylene blue [A. Bernthsen, Annalen der Chemie, 251, 1 (1888); I. Tomioka, J. Chem. Ind. Tokyo Japan, 20, I-2 (1917)].

Chart 2

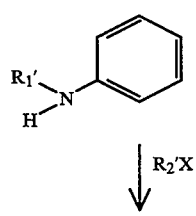

-continued
Chart 2

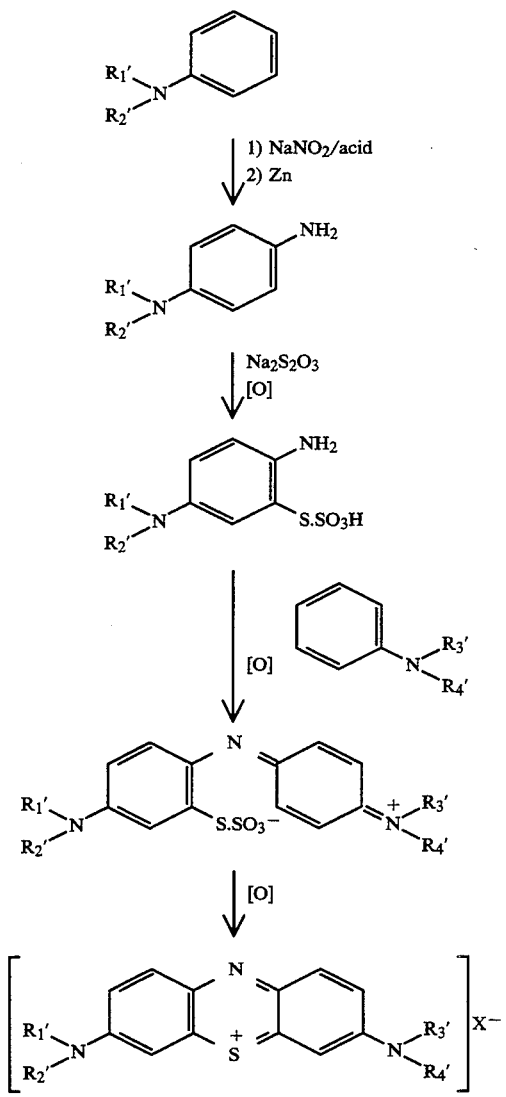

wherein at least one of $R_1'$, $R_2'$, $R_3$ and $R_4'$ is —($CH_2$)$_m$—CO—Y, the other groups are a $C_{1-6}$ alkyl group, Y is a leaving group and $X^-$ is a counter ion of the phenazathionium.

However, the synthetic intermediate of the compound of the present invention is much more lipophilic than methylene blue, and hence a satisfactory result is not obtained by mere application of the synthesis method of methylene blue wherein all the reaction solvents are water. Thus, as the reaction solvent, water or an organic solvent, especially acetonitrile or acetone is preferred. If necessary, the solvent is used in combination with them. As an oxidizing agent used in each oxidation step, a conventional inorganic oxidizing agent such as a dichromate, ferric chloride, manganese dioxide or the like can be used. As an oxidizing agent used in oxidation in a water-containing organic solvent which is characteristic of the present invention, a dichromate or manganese dioxide is preferred.

More detailed illustration of each step is set forth below.

A monoalkylaniline (wherein the alkyl is methyl or ethyl) is subjected to N-alkylation and nitrosation followed by reduction according to a conventional manner to obtain N,N-dialkyl-p-phenylenediamine. The N,N-dialkyl-p-phenylenediamine is reacted with a dichromate in an amount of 0.3 to 4.0 equivalents, preferably 0.3 to 2.0 equivalents in water or a water-containing organic solvent such as acetone, acetonitrile or the like in the presence of sodium thiosulfate in an amount of 1.2 to 3.5 equivalents, aluminum sulfate in an amount of 1.0 to 3.0 equivalents and an acid (e.g., hydrochloric acid, sulfuric acid or acid potassium hydrogen sulfate) in an amount of 8.0 to 12.0 equivalents at a reaction temperature of 0° to 40° C., preferably 5° to 25° C. to obtain the compound of the general formula (IV). This compound can be produced by using manganese dioxide in an amount of 3.0 to 10.0 equivalents instead of a dichromate.

The compound of the general formula (IV) is reacted with a dichromate in an amount of 0.6 to 3.0 equivalents, preferably 0.6 to 1.5 equivalents at 0 to 40° C, preferably 5 to 25° C in water, water-containing acetone or water-containing acetonitrile in the presence of the compound of the general formula (VIII) in an equivalent amount and an acid (e.g., hydrochloric acid, sulfuric acid or potassium hydrogen sulfate) in an amount of 1.0 to 3.0 equivalents to obtain an indaminthiosulfonic acid derivative of the general formula (III). Further, as an oxidizing agent to be used in this reaction, manganese dioxide in an amount of 3.0 to 10.0 equivalents can also be used.

The compound of the general formula (II) can be obtained by subjecting the indaminthiosulfonic acid derivative of the general formula (III) to oxidative ring closure with an inorganic oxidant in water, an organic solvent or a mixed solvent thereof. More specifically, the compound of the general formula (III) is treated in water, acetone, acetonitrile or a water-containing solvent thereof with manganese dioxide in an amount of 5.0 to 20.0 equivalents, preferably 10.0 to 15.0 equivalents, more preferably in the presence of a catalytic amount of copper sulfate at 20 to 100° C. to obtain the novel methylene blue derivative of the general formula (II). Furthermore, in the steps illustrated in the Chart 2, the compound (II) can be produced from the compound (IV) without isolating the intermediate (IV) and (III) by adding required reagents to the slurry of each step.

The compound of the present invention can be coupled to various proteins such as an antibody fragment, avidin (basic sugar protein) and the like. When the photosensitive dye derivative is used for treatment of cancer, it is necessary to select a protein or biomolecule which is required for the growth of cancer cells and readily taken up by cancer cells, such as transferrin protein (iron transport protein).

For this coupling, it takes 1 minute to 24 hours, preferably 4 to 12 hours. The coupling temperature is preferably 1° to 80° C. Although the coupling reaction is promoted at a higher temperature, heat denaturation of the protein is also caused. Therefore, normally, the temperature is suitably 1° to 24° C. The pH during the coupling is 4 to 10, preferably 6 to 8. Although, normally, the coupling reaction is carried out in an aqueous solution, there can also be used a solvent which does not have strong nucleophilicity and does not react with the reactive derivative such as alcohols, acetone and dimethylformamide. Likewise, any buffer salts for controlling the pH which does not react with the reactive derivatives can be used. For example, phosphates and the like are suitable, whereas tris(hydroxymethyl-)aminoethane and the like are not suitable.

Virtually all proteins have a primary amino group which can react with the compound of the present invention. When the compound of the present invention having a group which can react with an amino group is reacted with a compound having an amino group such as proteins, haptens or the like, the reaction is preferably carried out in the presence of a condensing agent in the case that the group which can react with an amino group above is a carboxyl group. Examples of the condensing agent include DCC, WSC and the like. It is necessary to ensure that no impurities having a mercapto group except reduced state of cysteine of a protein is present in a solution of the protein during its coupling to the maleimido derivative. An antibody protein is particularly recommended in the application to immunoassays or photodynamic therapy of cancer. The molar ratio of the reactive photosensitive dye derivative based on a protein during the coupling is more than 1, preferably 10 to 300.

After the reactive dye derivative is coupled to a protein, the protein-dye conjugate thus formed can be separated from the unreacted dye by, for example, gel filtration chromatography. The protein-dye conjugate thus prepared can be stored in an aqueous solution for a long period. In a higher pH region (above 10), however, the dye is unstable and cannot be stored.

The reactive dye derivative can be coupled to low molecular weight haptens such as medicaments or derivatives thereof, hormones or nucleic acids under the same conditions as those described above. The conjugate thus formed can be purified by means of chromatography and the like which can distinguish a product from unreacted reagents.

In the application of the protein-dye conjugate to immunoassays, the conjugate is irradiated with light of appropriate wavelength which can excite the dye, and oxidative chemiluminescence is detected which is produced by the product from the excited dye in combination with a sensitive reagent such as luminol according to a conventional manner.

When the protein-dye conjugate is used for photodynamic therapy of cancer, semiconductor laser light (670 nm) is especially preferred because light spectrum of the light source agrees well with absorption spectrum of the dye and it is readily available.

According to the photosensitive dye derivatives of the present invention, covalently coupling of antibody proteins and the like which has been difficult can be readily attained. Further, the protein-dye conjugate precipitation and nonspecific binding to the surface of a solid phase which is a problem in covalently coupling of antibody proteins and the like can be avoided.

The following Reference Examples and Examples further illustrate the present invention in detail but are not to be construed to limit the scope thereof.

REFERENCE EXAMPLE 1

N-(3-Ethoxycarbonylpropyl)-N-methyl-p-phenylenediamine

Ethyl 4-(N-methylanilino)butyrate (J.C.S. Perkin I, 1972, 1803) (22 g) was dissolved by addition of conc. hydrochloric acid (60 ml) under ice-cooling. To the solution was added a solution of sodium nitrite (8 g) in water (10 ml) dropwise at 0° to 4° C. with vigorous stirring. The mixture was stirred at the same temperature for 30 minutes. Then zinc powder (30 g) was added at below 10° C. The resulting mixture was further stirred for 30 minutes at 15° C. The zinc was filtered off. The filtrate was made alkaline with sodium bicarbonate and then was extracted with ether. The ether layer was dried over anhydrous sodium sulfate and concentrated. The residue was subjected to column chromatography on silica gel and developed with ethyl acetate/hexane (1:1) to obtain N-ethoxycarbonylpropyl-N-methyl-p-phenylenediamine (9 g).

NMR (CDCl$_3$) δ: 1.21 (3H, t, J=7Hz), 1.84 (2H, quintet, J=7Hz), 2.30 (2H, t, J=7Hz), 2.80 (3H, S), 3.1-3.5 (2H, hr.), 3.20 (2H, t, J=7HZ), 4.10 (2H, q, J=7Hz), 6.63 (4H, s).

IR (neat) ν: 3450, 3350, 1730, 1520, 1370, 1265, 1175, 815 cm$^{-1}$.

REFERENCE EXAMPLE 2

Ethyl 5-(N-methylanilino)valerate

A mixture of N-methylaniline (16 g) and ethyl 5-bromovalerate (30.2 g) was stirred at 110° C. for 22 hours. Then the mixture was made alkaline with an aqueous sodium bicarbonate. The resulting mixture was extracted with ethyl acetate, dried over anhydrous magnesium sulfate and concentrated. The residue was distilled under reduced pressure to obtain ethyl 5-(N-methylanilino)valerate (28.6 g).

b.p.: 124°-128° C./0.4 mmHg

NMR (CDCl$_3$) δ: 1.25 (3H, t, J=7.2Hz), 1.66 (4H, m), 2.33 (2H, t, J=8Hz), 2.91 (3H, s), 3.32 (2H, t, J=7Hz), 4.12 (2H, q, J=7.2Hz), 6.67 (3H, m), 7.22 (2H, m).

REFERENCE EXAMPLE 3

Ethyl 6-(N-methylanilino)hexanoate

A mixture of N-methylaniline (25 g) and ethyl 6-bromohexanoate (50 g) was stirred at 120° C. for 24 hours. After cooling, an aqueous sodium bicarbonate was added to make the mixture alkaline. Then the resulting mixture was extracted with ethyl acetate, washed with brine and dried over anhydrous sodium sulfate. The mixture was concentrated under reduced pressure and distilled to obtain ethyl 6-(N-methylanilino)hexanoate (40.5 g).

b.p.: 141°-143° C./0.9 mmHg

NMR (CDCl$_3$) δ: 1.25 (3H, t, J=7.2Hz), 1.37 (2H, m), 1.65 (4H, m), 2.30 (2H, t, J=7.4Hz), 2.92 (3H, s), 3.30 (2H, t, J=7.4Hz), 4.13 (2H, q, J=7.2Hz), 6.67 (3H, m), 7.22 (2H, m).

REFERENCE EXAMPLE 4

Tert-Butyl 4-chlorobutyrate

4-Chlorobutyryl chloride (14.1 g) was added dropwise with stirring under ice-cooling to a mixture of tert-butanol (18.5 g) and dimethylaniline (18.2 g). The resulting mixture was stirred for 2 hours in an oil bath (100° C.). Ether (200 ml), water (100 ml) and 1N hydrochloric acid (50 ml) were added to the reaction mixture and mixed with shaking. The organic layer was washed successively with 1N hydrochloric acid, an aqueous sodium bicarbonate and brine and dried over anhydrous magnesium sulfate. The solvent was distilled off and then the residue was subjected to distillation under reduced pressure to obtain tert-butyl 4-chlorobutyrate (13. 2 g).

b.p.: 94°-95° C./22 mmHg

NMR (CDCl$_3$) δ: 1.45 (9H, s), 2.05 (2H, quintet, J=7Hz), 2.41 (2H, t, J=7Hz), 3.59 (2H, t, J=7Hz).

REFERENCE EXAMPLE 5

Tert-Butyl 4-(N-methylanilino)butyrate

A mixture of tert-butyl 4-chlorobutyrate (10.72 g) obtained in Reference Example 4 and N-methylaniline (7.72 g) was stirred for 21 hours in an oil bath (100° C.). A saturated solution (50 ml) of sodium bicarbonate was added to the reaction mixture. The mixture was extracted with ether (300 ml), dried over anhydrous magnesium sulfate and concentrated. Then the residue was subjected to distillation under reduced pressure to obtain tert-butyl 4-(N-methylanilino)butyrate (4.40 g).

b.p.: 140°–147° C./1.5mmHg

NMR (CDCl$_3$) δ: 1.45 (9H,s), 1.86 (2H, quintet, J=7Hz), 2.26 (2H, t, J=7Hz), 2.92 (3H, s), 3.35 (2H, t, J=7Hz), 6.6–6.8 (3H, m), 7.1–7.3 (2H, m).

REFERENCE EXAMPLE 6

N-(3-tert-Butoxycarbonylpropyl)-N-methyl-p-phenylenediamine

Tert-Butyl 4-(N-methylanilino)butyrate (8.00 g) obtained in Reference Example 5 was dissolved in 80% acetic acid (30 ml). To the solution was added dropwise a solution of sodium nitrite (2.44 g) in water (3 ml) with stirring at below 10° C. The resulting mixture was stirred for 30 minutes at the same temperature. Then acetic acid (30 ml) was added and zinc powder (19 g) was added at below 10° C. The resulting mixture was stirred for 30 minutes and then filtered. The filtrate was concentrated under reduced pressure and mixed with an aqueous sodium bicarbonate and ether with shaking. The ether layer was dried over anhydrous magnesium sulfate and concentrated under reduced pressure. The residue was subjected to column chromatography on silica gel and eluted with hexane/ethyl acetate (2:1) to obtain N-tert-butoxycarbonylpropyl-N-methyl-p-phenylenediamine (3.21 g) as brown oil.

NMR (CDCl$_3$) δ: 1.44 (9H, s), 1.81 (2H, quintet, J=7Hz), 2.55 (2H, t, J=7Hz), 2.50–3.50 (2H, br.), 2.80 (3H, s), 3.19 (2H, t, J=7Hz), 6.65 (4H, s).

REFERENCE EXAMPLE 7

3-[N-(4-Ethoxycarbonylbutyl)-N-methylamino]-7-dimethylaminophenazathionium chloride Ethyl 5-(N-methylanilino)valerate (0.25 g) obtained in Reference Example 2 was dissolved by addition of 1N hydrochloric acid (1 ml) and water (14 ml) under ice-cooling. Then 2-amino-5-dimethylaminophenylthiosulfonic acid [Ann. Chem., 251, 1 (1988)](0.25 g) was added. A solution of sodium dichromate 2 hydrate (0.2 g) in water (2 ml) was added dropwise at 5 to 10° C. and the mixture was stirred at the same temperature for 30 minutes. Acetic acid (0.03 ml) was added to the reaction mixture. The resulting mixture was stirred at room temperature for additional 1 hour. The resulting precipitate was filtered and washed with water. Then the precipitate was suspended in acetonitrile (20 ml). Manganese dioxide (0.25 g) and catalytic amount of copper sulfate were added and resulting mixture was heated under reflux for 30 minutes. The reaction mixture was filtered and the filtrate was concentrated to dryness under reduced pressure. The residue was subjected to column chromatography on silica gel and eluted with acetonitrile followed by a mixed solvent of CH$_3$CN/H$_2$O/1N HCl (40:5:1) to obtain 3-[N-(4-ethoxycarbonyl-butyl)-N-methylamino]-7-dimethylaminophenazathionium chloride (0.29 g).

NMR (D$_2$O) δ: 1.28 (3H, t), 1.67 (4H, m), 2.48 (2H, m), 3o17 (9H, hr. s), 3.55 (2H, m), 4.20 (2H, q), 6.80–7.50 (6H, m).

IR (KBr) ν: 3420 (br.), 1725, 1600, 1490, 1440, 1390, 1340, 1245, 1180, 1140, 885 cm$^{-1}$.

REFERENCE EXAMPLE 8

3-[N-(4-Ethoxycarbonylbutyl)-N-methylamino]-7-dimethylaminophenazathionium chloride Ethyl 5-(N-methylanilino)valerate (0.2 g) obtained in Reference Example 2 was dissolved in 50% acetonitril-water (10 ml). Acetic acid (0.1 ml), 2-amino-5-dimethylaminophenylthiosulfonic acid (0.2 g) and manganese dioxide (0.5 g) were added. The mixture was stirred at room temperature for 2 hours and further at 80° C. for 5 hours. Then the reaction mixture was filtered and washed with acetonitrile. The filtrate was concentrated to dryness under reduced pressure. The residue was subjected to column chromatography on silica gel and eluted with CH$_3$CN followed by CH$_3$CN/H$_2$O/1N HCl (40:5:1) to obtain 3-[N-(4-ethoxy-carbonylbutyl)-N-methylamino]-7-dimethylaminophenazathionium chloride (0.11 g).

REFERENCE EXAMPLE 9

3-[N-(4-Carboxybutyl)-N-methylamino]-7-dimethylaminophenazathionium chloride 3-[N-(4-Ethoxycarbonylbutyl)-N-methylamino]-7-dimethylaminophenazathionium chloride (0.7 g) was dissolved in 1N hydrochloric acid (10 ml). The mixture was allowed to react at room temperature for 48 hours. The reaction mixture was subjected to column chromatography on silica gel and eluted successively with water, CH$_3$CN/H$_2$O (10:1) and CH$_3$CN/H$_2$O/1N HCl (40: 5: 1). The desired fraction was concentrated and then lyophilized to obtain 3-[N-(4-carboxybutyl)-N-methylamino]-7-dimethylaminophenazathionium chloride (0.7 g).

NMR (D$_2$O) δ: 1.67 (4H, hr. s), 2.49 (2H, hr. s), 3.08 (9H, br. s), 3.45 (2H, br. s), 6.60–7.40 (6H, m).

IR (KBr) ν: 3650–2800, 1720, 1600, 1485, 1390, 1335, 885 cm$^{-1}$.

EXAMPLE 1

3-[N-Methyl-N-(4-succinimidoxycarbonylbutyl)-amino]-7-dimethylaminophenazathionium chloride 3-[N-(4-Carboxybutyl)-N-methylamino]-7-dimethylamino phenazathionium chloride (0.34 g) obtained in Reference Example 9 was dissolved in dimethylformamide (100 ml). The mixture was concentrated to about 30 ml under reduced pressure. Then N-hydroxysuccinimide (0.255 g) and WSC (0.425 g) were added and the mixture was allowed to react at room temperature for 3 days. The solvent was distilled off under reduced pressure. The residue was then dissolved in dichloromethane, washed with saturated brine and dried over anhydrous sodium sulfate. The mixture was concentrated under reduced pressure and the residue was dissolved by addition of dichloromethane (6 ml). Then ethyl acetate (100 ml) was added. The resulting precipitate was filtered off and dried to obtain 3-[N-methyl-N-(4-succinimidoxy-carbonylbutyl)amino]-7-dimethylaminophenazathionium chloride (0.2 g).

NMR (DMSO-d6) δ: 1.74 (4H, hr. s), 2.77 (2H, hr. s), 2.82 (4H, s), 3.33 (3H, s), 3.38 (6H, s), 3.77 (2H, hr. s), 7.45–7.60 (4H, m), 7.80–7.98 (2H, m).

IR (KBr) ν: 3425 (br.), 1810, 1780, 1735, 1600, 1395, 1355 (shoulder), 1340, 855 cm$^{-1}$.

REFERENCE EXAMPLE 10

3-[N-(5-Ethoxycarbonylpentyl)-N-methylamino]-7-dimethylaminophenazathionium chloride Ethyl 6-(N-methylanilino)hexanoate (1 g) obtained in Reference Example 3 was dissolved by addition of 1N hydrochloric acid (4 ml) and water (50 ml) under ice-cooling. Then 2-amino-5-dimethylaminophenylthiosultonic acid (1 g) was added. To the mixture was added dropwise a solution of sodium dichromate 2 hydrate (0.8 g) in water (6 ml) at 5° to 10° C. The mixture was stirred at the same temperature for 30 minutes and further at room temperature for 1 hour. The resulting precipitate was filtered, washed with water and suspended in acetonitrile (80 ml). Manganese dioxide (1 g) and catalytic amount of copper sulfate were added and the resulting mixture was heated under reflux for 1 hour. The reaction mixture was filtered. The residue was washed with methanol and then the filtrate was concentrated to dryness under reduced pressure. The residue was subjected to column chromatography on silica gel and eluted with $CH_3CN$ followed by $CH_3CN/H_2O$/1N HCl (40:5:1). The desired fraction was lyophilized to obtain 3-[N-(5-ethoxycarbonylpentyl)-N-methylamino]-7-dimethylamino-phenazathionium chloride (0.875 g).

NMR (CDCl$_3$) δ: 1.26 (3H, t, J=7Hz), 1.49 (2H, m), 1.74 (4H, m), 2.35 (2H, t, J=7.2 Hz), 3.46 (6H, s), 3.71 (2H, br. t), 4.13 (2H, q, J=7Hz), 7.28 (2H, m), 7.00–8.00 (4H, m).

IR (KBr) ν: 3425 (br.), 1725, 1600, 1490, 1390, 1335, 1245, 1175, 1140, 885 cm$^{-1}$.

EXAMPLE 2

3-[N-Methyl-N-(5-succinimidoxycarbonylpentyl)amino]-7-dimethylaminophenazathionium chloride 3-[N-(5-Ethoxycarbonylpentyl)-N-methylamino]-7-dimethylaminophenazathionium chloride (0.785 g) obtained in Reference Example 10 was dissolved in 1N hydrochloric acid (10 ml) and the mixture was allowed to react at room temperature for 16 hours. The reaction mixture was subjected to column chromatography on silica gel and eluted successively with water, $CH_3CN/H_2O$/1N HCl (40:5:1). The desired fraction was lyophilized. The residue was dissolved in dimethylformamide (200 ml). Insoluble materials were filtered off and then the filtrate was concentrated to about 50 ml. To this solution was added N-hydroxysuccinimide (0.54 g) and WSC (0.9 g). The mixture was allowed to react at room temperature for 48 hours. The reaction mixture was concentrated under reduced pressure and then the residue was dissolved in dichloromethane. The solution was washed with saturated brine, dried over anhydrous sodium sulfate and concentrated under reduced pressure. The resulting residue was dissolved in dichloromethane (15 ml) and ethyl acetate (250 ml) was added thereto. The resulting precipitate was filtered and dried to obtain 3-[N-methyl-N-(5-succinimidoxycarbonylpentyl)-amino] -7-dimethylaminophenazathionium chloride (0.718 g).

NMR (CDCl$_3$) δ: 1.56 (2H, m), 1.83 (4H, m), 2.66 (2H, t, J=6.8Hz), 2.91 (4H, s), 3.40 (3H, s), 3.46 (6H, s), 3.73 (2H, m), 7.20–8.00 (6H, m).

IR (KBr) ν: 3425, 1810, 1780, 1735, 1600, 1390, 1335, 1210, 140, 1070, 885 cm$^{1}$.

REFERENCE EXAMPLE 11

3-[N-(3-tert-Butoxycarbonylpropyl)-N-methylamino]-7-dimethylaminophenazathionium chloride Tert-Butyl 4-(N-methylanilino)butyrate (0.50 g) obtained in Reference Example 5 was dissolved by addition of a solution of potassium hydrogensulfate (0.41 g) in water (25 ml) under ice-cooling. To this solution was added 2-amino-5-dimethylaminophenylthiosulfonic acid (0.50 g). A suspension of sodium dichromate 2 hydrate (0.40 g) in water (5 ml) was added dropwise at 5° to 10° C. Then acetic acid (0.06 ml) was added and the resulting mixture was stirred at the same temperature for 30 minutes. Further, it was allowed to react at room temperature for 1.5 hours. The reaction mixture was filtered and washed with water. Then the residue was suspended in acetone. Manganese dioxide (4.0 g) and copper sulfate (0.03 g) were added thereto and the mixture was heated under reflux for 1 hour. The reaction mixture was filtered and concentrated to dryness. The crude product thus obtained was subjected to column chromatography on silica gel and eluted with $CH_3CN$, 90% $CH_3CN$-$H_2O$ and $CH_3CN/H_2O$/1N HCl (30:5:3) to obtain 3-[N-(3-tert-butoxycarbonylpropyl)-N-methylamino]-7-dimethylaminophenazathionium chloride (0.33 g).

m.p.: 94°–98° C. (dec.)

NMR (D$_2$O) δ: 1.52 (9H, s), 1.87 (2H, m), 2.43 (2H, t, J=7Hz), 3.13 (3H, s), 3.17 (6H,s), 3.47 (2H, m), 6.81 (2H, hr. s), 7.0–7.1 (2H, m), 7.25–7.4 (2H, m).

IR (KBr) ν: 3380, 1720, 1600, 1390, 1335, 1140, 885, 615 cm$^{-1}$.

λ max: 651 nm (in MeOH)

Elemental Analysis for $C_{23}H_{30}N_3O_2SCl\cdot 2H_2O$, Calcd.: C, 57.07; H, 7.08; N, 8.68; Found : C, 57.08; H, 6.70; N, 8.70.

REFERENCE EXAMPLE 12

3-[N-(3-Carboxypropyl)-N-methylamino]-7-dimethylaminophenazathionium chloride

3-[N-(3-tert-Butoxycarbonylpropyl)-N-methylamino]-7-dimethylaminophenazathionium chloride (0.05 g) obtained in Reference Example 11 was dissolved in trifluoroacetic acid (3 ml). The mixture was allowed to react at room temperature for 1 hour. Trifluoroacetic acid was distilled off under reduced pressure. Then the residue was subjected to column chromatography on silica gel and eluted with $CH_3CN$ followed by $CH_3CN/H_2O$/1N HCl (30:5:3) to obtain 3-[N-(3-carboxypropyl)-N-methylamino]-7-dimethylaminophenazathionium chloride (0.014 g).

NMR (D$_2$O) δ: 1.79 (2H, m), 2.51 (2H, m), 3.00 (9H, hr. s), 3.31 (2H, m), 6.55–7.10 (6H, m).

IR (KBr) ν: 3420, 1605, 1395, 1340, 1140, 885, 850, 800 cm$^{-1}$.

EXAMPLE 3

3-[N-Methyl-N-(3-succinimidoxycarbonylpropyl)amino]-7-dimethylaminophenazathionium chloride Trifluoroacetic acid (15 ml) was added to 3-[N-(3-tert-butoxycarbonylpropyl)-N-methylamino]-7-dimethyl-aminophenazathionium chloride (0.17 g) obtained in Reference Example 11. The mixture was allowed to react at room temperature for 15 minutes. Trifluoroacetic acid was distilled off under reduced pressure and the residue was dissolved in acetonitrile (10 ml). Pyridine (0.19 ml) and DSO (0.32 g) were added thereto and the mixture was stirred at room temperature for 1.5 hours. The reaction mixture was concentrated to dryness. The residue was then dissolved in dichloromethane (50 ml). The resulting solution was mixed with saturated brine containing 1N HCl (5 ml) with shaking. Further, the mixture was washed with saturated brine, dried over anhydrous sodium sulfate and concentrated under reduced pressure. The residue was dissolved in dichloromethane and an excess amount of ethyl acetate was added thereto to form precipitate. The precipitate thus obtained was filtered off and dried to obtain 3-[N-methyl-N-( 3-succinimidoxycarbonylpropyl)amino]-7-dimethylaminophenazathionium chloride (0.12 g).

m.p.: 125°–130° C. (dec.)

NMR (CDCl$_3$) δ: 2.11 (2H, m), 2.81 (2H, t, J=6Hz), 2.91 (4H, s), 3.37 (9H, br. s), 3.79 (2H, m), 7.23 (2H, d, J=9Hz), 7.75 (2H, d, J=9Hz), 7.76 (2H, m).

IR (KBr) ν: 3420, 1810, 1790, 1735, 1600, 1390, 1340, 1140, 885 cm$^{-1}$.

REFERENCE EXAMPLE 13

2-Amino-5-[N-(3-ethoxycarbonylpropyl)-N-methylamino]phenylthiosulfonic acid

N-(3-Ethoxycarbonylpropyl)-N-methyl-p-phenylenediamine (8.97 g) obtained in Reference Example 1 was dissolved by addition of 1N sulfuric acid (76 ml) under ice-cooling. A solution of aluminium potassium sulfate 12 hydrate (17.1 g) in water (80 ml) and a solution of sodium thiosulfate 5 hydrate (9.88 g) in water (19 ml) were added at below 10° C. Then a solution of potassium dichromate (3.65 g) in water (57 ml) was added dropwise at 10° C. The cooling bath was removed and the mixture was stirred at room temperature for 1 hour. Then sodium bicarbonate was added to adjust the resulting mixture to pH 5. The reaction mixture was filtered and the filtrate was concentrated to dryness under reduced pressure. The residue was subjected to ODS (wherein octadecyl group is chemically bound to silanol of silica gel) column chromatography and eluted with 50% MeOH-H$_2$O. The desired fraction was lyophilized to obtain 2-amino-5-[N-(3-ethoxycarbonylpropyl)-N-methylamino]phenylthiosulfonic acid (4 g).

NMR (CH3OD) δ: 1.22 (3H, t, J=7Hz), 1.80 (2H, quintet, J=7Hz), 2.35 (2H, t, J=7Hz), 2.96 (3H, s), 3.30 (2H, t, J=7Hz), 4.10 (2H, q, J=7Hz), 6.96 (2H, br. s), 7.23 (1H, hr. s).

IR (KBr) ν: 1730, 1625, 1505, 1220, 1030, 835 cm$^{-1}$.

REFERENCE EXAMPLE 14

[N-(3-tert-Butoxycarbonylpropyl)-N-methylamino]-[N'-(3-ethoxycarbonylpropyl)-N'-methylamino]-indaminthiosulfonic acid Tert-Butyl 4-(N-methylanilino)butyrate (0.997 g) obtained in Reference Example 5 was dissolved by addition of a solution of potassium hydrogensulfate (0.817 g) in water (10 ml) under ice-cooling. To this solution was added 2-amino-5-[N-(3-ethoxycarbonylpropyl)-N-methylamino]-phenylthiosulfonic acid (1.394 g) obtained in Reference Example 13. Then potassium dichromate (1.18 g) was added portionwise and the mixture was stirred at 5° to 10° C. for 1 hour. The resulting precipitate was filtered, washed with water and dissolved in methanol. Insoluble materials were filtered off and the filtrate was concentrated under reduced pressure. The concentrate was subjected to ODS column chromatography and eluted with 50% CH$_3$CN-H$_2$O to obtain [N-( 3-tert-butoxycarbonylpropyl)-N-methylamino]-[N'-(3-ethoxycarbonylpropyl)-N'-methylamino]indaminthiosulfonic acid.

IR (KBr) ν: 3450, 3350, 1730, 1610, 1515, 1365, 1240, 1170, 1015, 820, 615 cm$^{-1}$.

REFERENCE EXAMPLE 15

3-[N-(3-tert-Butoxycarbonylpropyl)-N-methylamino]-7-[N-(3-ethoxycarbonylpropyl)-N-methylamino]-phenazathionium chloride

[N-(3-tert-butoxycarbonylpropyl)-N-methylamino]-[N'-(3-ethoxycarbonylpropyl)-N'-methylamino]indamin-thiosulfonic acid (0.60 g) obtained in Reference Example 14 was dissolved in acetone (25 ml). Manganese dioxide (3 g) was added thereto and the mixture was stirred at room temperature for 20 hours. Manganese dioxide was filtered off and washed with methanol. The filtrate was concentrated under reduced pressure. The residue was subjected to column chromatography on silica gel and eluted with CH$_3$CN/H$_2$O (20:1) followed by CH$_3$CN/H$_2$O/1N HCl (120:20:3). The desired fractions were collected and concentrated to obtain 3-[N-(3-tert-butoxycarbonylpropyl)-N-methylamino]-7-[N-(3-ethoxycarbonylpropyl)-N-methylamino]phenazathionium chloride (0.26 g).

NMR (D$_2$O) δ: 1.30 (3H, t, J=7Hz), 1.50 (9H, s), 1.83–1.90 (2H, br.), 2.38–2.55 (2H, m), 3.15 (6H, br. s), 3.47 (2H, br. s), 4.20 (2H, q, J=7Hz), 6.85 (2H, br. s), 7.11 (2H, m), 7.65 (2H, m).

IR (KBr) ν: 1725, 1600, 1400, 1365, 1340, 1185, 1150, 890 cm$^{-1}$.

EXAMPLE 4

3-[N-(3-Succinimidoxycarbonylpropyl)-N-methylamino]-7-[N-(3-ethoxycarbonylpropyl)-N-methylamino]phenazathionium chloride Trifluoroacetic acid (18 ml) was added to 3-[N-(3-tert-butoxycarbonylpropyl)-N-methylamino]-7-[N-(3-ethoxycarbonylpropyl)-N-methylamino]phenazathionium chloride (0.24 g) obtained in Reference Example 15 and the mixture was stirred at room temperature for 1 hour. The reaction mixture was concentrated to dryness under reduced pressure. Acetonitrile (15 ml), pyridine (0.33 ml) and DSC (0.52 g) were added to the residue and the resulting mixture was stirred at room temperature for 2 hours. The reaction mixture was concentrated under reduced pressure. The residue was dissolved in dichloromethane (150 ml), washed with saturated brine containing 1N hydrochloric acid (6 ml), further washed with saturated brine, dried over anhydrous sodium sulfate and concentrated to dryness. The resulting residue was re-precipitated from dichloromethane-ethyl acetate to obtain 3-[N-(3-succinimidoxycarbonyl propyl)-N-methylamino]-7-[N-(3-ethoxycarbonylpropyl)-N-methylamino]phenazathionium chloride (0.18 g).

m.p. : 70°–85° C. (dec.)

NMR (CDCl$_3$) δ: 1.27 (3H, t, J=7Hz), 2.04 (2H, m), 2.18 (2H, m), 2.53 (2H, t, J=6.5Hz), 2.89 (2H,m), 2.97 (4H, s), 3.40 (3H,s), 3.42 (3H, s), 3.83 (4H, m), 4.16 (2H, q, J=7Hz), 7.36 (2H, t, J=10Hz), 7.59 (2H, d, J=15Hz), 7.85 (2H, dd, J=2.10 Hz).

IR (KBr) $\nu$: 3420, 1810, 1780, 1735, 1595, 1390, 1335, 1190, 1140, 885 cm$^{-1}$.

REFERENCE EXAMPLE 16

2-Amino-5-[N-(3-tert-butoxycarbonylpropyl)-N-methylamino]phenylthiosulfonic acid N-(3-tert-butoxycarbonylpropyl)-N-methyl-p-phenylenediamine (3.30 g) obtained in Reference Example 6 was dissolved in 1N sulfuric acid (50 ml) under ice-cooling. A solution of aluminum sulfate 14-18 hydrate (8.33 g) in water (15 ml), a solution of sodium thiosulfate 5 hydrate (9.31 g) in water (15 ml) and a solution of potassium dichromate 2 hydrate (1.27 g) in water (17 ml) were added successively at the reaction temperature of 5° to 10° C. The resulting mixture was stirred at the same temperature for 30 minutes and then at room temperature for additional 1 hour. Sodium bicarbonate was added to the reaction mixture to adjust to pH 4 and the reaction mixture was concentrated to dryness under reduced pressure. Methanol (500 ml) was added to the concentrate and insoluble materials were filtered off. The filtrate was concentrated under reduced pressure. The residue was subjected to column chromatography on silica gel and eluted with ethyl acetate/methanol (15:1) followed by the same solvent system (5:1) to obtain 2-amino-5-[N-(3-tert-butoxycarbonylpropyl)-N-methylamino]phenylthiosulfonic acid (1.54 g) as a dark green viscous material.

NMR (CDCl$_3$) $\delta$: 1.42 (9H, s), 1.73 (2H, m), 2.19 (2H, br. s), 2.76 (3H, hr. s), 3.15 (2H, br. m), 4.50 (3H, hr. s), 6.50–7.40 (3H, m).

REFERENCE EXAMPLE 17

Bis[N-(3-tert-butoxycarbonylpropyl)-N-methylamino]indaminthiosulfonic acid

Tert-Butyl 4-(N-methylanilino) butyrate (1.16 g) obtained Reference Example 5 was dissolved in a solution of potassium hydrogensulfate (0.95 g) in water (90 ml). Then 2-amino-5-[N-(3-tert-butoxycarbonylpropyl)-N-methylamino]-phenylthiosulfonic acid (1.62 g) obtained in Reference Example 16 was added thereto under ice-cooling. A solution of potassium dichromate 2 hydrate (1.38 g) in water (10 ml) was added dropwise at 5° to 10° C. Acetic acid (0.14 ml) was added and the mixture was stirred at room temperature for 1 hour. The resulting precipitate was filtered off and washed with water. The filtration residue was extracted with methanol (200 ml) and concentrated to dryness. The residue was subjected to column chromatography on silica gel and eluted with chloroform/methanol (20:1) to obtain bis[N-(3-tert-butoxycarbonylpropyl)-N-methylamino]indaminthiosulfonic acid (0.48 g).

NMR (CDCl$_3$) $\delta$: 1.45 (18H, s), 1.88 (4H, br.), 2.86 (4H, br. s), 2.90–3.20 (4H, m), 3.20–3.70 (6H, br.), 6.50–7.70 (7H, m).

REFERENCE EXAMPLE 18

3,7-Bis[N-(3-tert-butoxycarbonylpropyl)-N-methylamino]phenazathionium chloride

Bis[N-(3-tert-butoxycarbonylpropyl)-N-methylamino]indaminthiosulfonic acid (0.47 g) obtained in Reference Example 17 was dissolved in acetone (40 ml). Manganese dioxide (2.0 g) and copper sulfate (0.03 g) were added and the mixture was heated under reflux for 30 minutes. The reaction mixture was filtered and the filtrate was concentrated to dryness under reduced pressure. The residue was subjected to column chromatography on silica gel and eluted successively with CH$_3$CN, 90% CH$_3$CN-H$_2$O and CH$_3$CN/H$_2$O/1N HCl (120:20:3). The desired fraction was concentrated to dryness. The residue was re-precipitated from dichloromethane-ethyl acetate to obtain 3,7-bis[N-(3-tert-butoxycarbonylpropyl)-N-methyl-amino]phenazathionium chloride (0.11 g).

m.p. : 142°–145° C.

NMR (CDCl$_3$) $\delta$: 1.47 (18H, s), 2.00 (4H, quintet, J=7Hz), 2.43 (4H, t, J=7Hz), 3.43 (6H, s), 3.79 (4H, t, J=7Hz), 7.39 (2H, d, J=10Hz), 7.62 (2H, br. s), 7.91 (2H, s J=10Hz).

IR (KBr) $\nu$: 3430, 2970, 2920, 1720, 1595, 1395, 1335, 1240, 1140, 980 cm$^{-1}$.

Elemental Analysis for C$_{30}$H$_{42}$N$_3$O$_4$SCl$\cdot$3H$_2$O, Calcd.: C, 57.17; H, 7.68; N, 6.67 Found : C, 57.29; H, 7.45; N, 6.67

REFERENCE EXAMPLE 19

3,7-Bis[N-(3-carboxypropyl)-N-methylamino]-phenazathionium chloride 3,7-Bis[N-(3-tert-butoxycarbonylpropyl)-N-methylamino]phenazathionium chloride (0.11 g) obtained in Reference Example 18 was dissolved in trifluoroacetic acid (10 ml). The mixture was allowed to react at room temperature for 30 minutes. Then the reaction mixture was concentrated to dryness under reduced pressure to obtain 3,7-bis[N-(3-carboxypropyl)-N-methylamino]phenazathionium chloride quantitatively as its trifluoroacetate.

NMR (D$_2$O) $\delta$: 1.86 (4H, br. s), 2.45 (4H, br. s), 2.80–3.70 (10 H, br. m), 6.70–7.40 (6H, br. m).

EXAMPLE 5

3,7-Bis[N-methyl-N-(3-succinimidoxycarbonylpropyl)amino]phenazathionium chloride and 3-[N-methyl-N-(3-succinimidoxycarbonylpropyl)amino]-7-[N-(3-carboxypropyl)-N-methylamino]-phenazathionium chloride 3,7-Bis[N-(3-carboxypropyl)-N-methylamino]-phenazathionium chloride trifluoroacetate (0.11 g) obtained in Reference Example 19 was dissolved in acetonitrile (20 ml). Pyridine (0.14 ml) and DSC (0.21 g) were added and the resulting mixture was stirred at room temperature for 3 hours. The reaction mixture was concentrated under reduced pressure and then the residue was dissolved by addition of dichloromethane. The solution was washed with saturated brine, dried over anhydrous sodium sulfate and concentrated to dryness to obtain dark blue powder. The powder thus obtained was subjected to Sephadex ® LH-20 column chromatography and eluted with acetonitrile. The fractions were concentrated to dryness respectively to obtain a bissuccinimido ester derivative, 3,7-bis[N-(3-succinimidoxycarbonylpropyl)amino]phenazathionium chloride (0.1 g) from the firstly eluted fraction, and a monosuccinimido ester derivative, 3-[N-methyl-N-(3-succinimidoxycarbonylpropyl)amino]-7-[N-(3-carboxypropyl)-N-methylamino]phenazathionium chloride (0.03 g) from the subsequently eluted fraction.

BISSUCCINIMIDO ESTER m.p. : 115°–120° C. (dec.)

NMR (DMSO-d$_6$) $\delta$: 1.88 (2H, m), 2.02 (2H, m), 2.38 (2H, t, J=7Hz), 2.87 (4H, s), 3.13 (2H, t, J=7Hz), ca. 3.30 (3H, s), 3.36 (3H, s), 3.76 (4H, m), 7.55 (4H, br. s), 7.95 (2H, d, J=10Hz).

IR (KBr) ν: 3410, 2930, 1810, 1775, 1735, 1595, 1390, 1335, 1190, 1140, 880 cm⁻¹.

MONOSUCCINIMIDO ESTER m.p. 129°–133° C. (dec.)

NMR (DMSO-d₆) δ: 2.01 (4H, m), 2.84 (4H, s), 2.88 (4H, t, J=7Hz), ca. 3.30 (6H, s), 3.80 (4H, m), 7.56 (4H, hr. s), 7.96 (2H, d, J=10Hz).

IR (KBr) ν: 3400, 2930, 1810, 1775, 1730, 1595, 1390, 1335, 1990, 1140, 1065, 880 cm⁻¹.

EXAMPLE 6

3-[N-Methyl-N-(3-succinimidoxycarbonylpropyl)amino]-7-[N-[3-(1,3-dicarboxypropylcarbamoyl)propyl]-N-methylamino]phenazathionium chloride 3,7-Bis[N-methyl-N-(3-succinimidoxycarbonylpropyl)amino]phenazathionium chloride (20 mg) obtained in Example 5 was dissolved in acetonitrile (2 ml). Glutamic acid (8 mg), triethylamine (15 pl) and a solution of 50% acetonitrile-water (2 ml) were added. The resulting mixture was stirred for 10 minutes at room temperature. 1N hydrochloric acid (0.1 ml) was added to the reaction mixture. Then the mixture was subjected to Sephadex ® LH-20 column chromatography and eluted with acetonitrile. The desired fraction was concentrated to dryness to obtain 3-[N-methyl-N-(3-succinimidoxycarbonylpropyl)amino]-7-[N-[3-(1,3-dicarboxypropylcabamoyl)propyl]-N-methylamino]phenazathionium chloride (10.8 mg) as blue powder.

NMR (DMSO-d₆) δ: 1.75–2.05 (6H, m), 2.20–2.35 (4H, m), 2.84 (4H, s), 2.85–2.95 (2H, m), 3.60–3.85 (6H, m), 4.15–4.30 (1H, m), 7.50–7.60 (3H, m), 7.90–8.10 (3H, m).

IR (KBr) ν: 3420, 2970, 2940, 2670, 2490, 1810, 1735, 1660, 1595, 1390, 1340, 1145, 1035, 880 cm⁻¹.

REFERENCE EXAMPLE 20

N-(5-Ethoxycarbonylpentyl)-N-methyl-p-phenylenediamine

N-(5-Ethoxycarbonylpentyl)-N-methylaniline (10 g) obtained in Reference Example 3 was dissolved in 80% acetic acid (41.3 ml). A solution of sodium nitrite (3.05 g) in water (3.8 ml) was added thereto with stirring at below 10° C. Then acetic acid (37.5 ml) was added to the reaction mixture and zinc powder (23.8 g) was added over about 40 minutes, while keeping the mixture at below 0° C. The reaction mixture was poured into ice water (200 ml). The resulting mixture was filtered and the zinc powder was washed with ethyl acetate. The filtrate was extracted with ethyl acetate and the extract was neutralized with an aqueous sodium bicarbonate, washed with saturated brine, dried over anhydrous magnesium sulfate and concentrated under reduced pressure. The residue was subjected to column chromatography on silica gel and eluted with hexane/ethyl acetate (2:1) to obtain the desired compound (2.76 g) as purplish red viscous oil.

NMR (CDCl₃) δ (ppm): 1.25 (3H, t, J=7.0Hz), 1.33 (2H, quintet, J=7.5Hz), 1.54 (2H, quintet, J=7.5Hz), 1.65 (2H, quintet, J=7.5Hz), 2.29 (2H, t, J=7.5Hz), 2.80 (3H,s), 2.90–3.50 (2H, br.), 3.16 (2H, t, J=7.5Hz), 4.12 (2H, q, J=7.0Hz), 6.65 (5H, s).

IR (neat) ν: 3430, 3350, 2930, 1730, 1515, 1260, 1175, 810 cm⁻¹.

REFERENCE EXAMPLE 21

3,7-Bis[N-(5-ethoxycarbonylpentyl)-N-methylamino]phenazathionium chloride

N-(5-Ethoxycarbonylpentyl)-N-methyl-p-phenylenediamine (1.32 g) was dissolved in water (65 ml) containing sulfuric acid (0.75 g). A solution of sodium thiosulfate 5 hydrate (2.18 g) in water (5 ml) and manganese dioxide (0.86 g) were added with stirring under ice-cooling. After 20 minutes, additional sodium thiosulfate ½ hydrate (4.36 g) and manganese dioxide (1.92 g) were added and the resulting mixture was stirred for 1 hour. The reaction mixture was adjusted to pH 4 with 1N sulfuric acid. A solution of N-(5-ethoxycarbonylpentyl)-N-methylaniline (1.70 g) in 1N sulfuric acid (10 ml) was added at the same temperature. Further, additional manganese dioxide (2.08 g) and 25% sulfuric acid (6 ml) was added and the mixture was stirred for 1.5 hours. Then the reaction mixture was adjusted to pH 5 with 1N sodium hydroxide. Manganese dioxide (0.77 g) and copper sulfate (0.29 g) were added and the resulting mixture was stirred at 90° C. for 40 minutes. The reaction mixture was filtered. The residue was washed with water and then extracted with acetone (300 ml). The solution extracted with acetone was concentrated. The residue was extracted with chloroform and dried over anhydrous sodium sulfate. After concentration, the residue was subjected to column chromatography on silica gel and eluted successively with CH₃CN, 90% CH₃CN-H₂O and CH₃CN/H₂O/1N HCl (120:20:3) to obtain the desired compound (30 mg).

NMR (CDCl₃) δ (ppm): 1.26 (6H, t, J=7.0Hz), 1.50 (4H, m), 1.72 (4H, m), 2.35 (4H, t, J=7.0Hz), 3.41 (6H, s), 3.71 (4H, m), 4.13 (4H, q, J=7.0Hz), 7.23 (2H, br. d, J=9.0Hz), 7.80 (2H, br. s), 7.91 (2H, br. d, J=9.0Hz).

IR (KBr) ν: 1720, 1600, 1395, 1340, 1140, 885 cm⁻¹.

REFERENCE EXAMPLE 22

3,7-Bis[N-(5-carboxypentyl)-N-methylamino]phenazathionium chloride 3,7-Bis[N-(5-ethoxycarbonylpentyl)-N-methylamino]phenazathionium chloride (0.32 g) was dissolved in 90% acetonitrile (20 ml). 1N Hydrochloric acid (40 ml) was added to this solution and the resulting mixture was stirred at room temperature for 20 hours. The reaction mixture was concentrated under reduced pressure. The residue was subjected to column chromatography on silica gel and eluted successively with 90% CH₃CN-H₂O and CH₃CN/H₂O/1N HCl (30:5:1) to obtain the desired compound (0.32 g) as deep blue powder.

NMR (DMSO-d₆) δ (ppm): 1.25–1.50 (4H, m), 1.50–1.75 (8H, m), 2.24 (4H, t, J=7.0Hz), 3.50 (6H, s), 3.65–3.80 (4H, m), 7.35–7.50 (2H, m), 7.54 (2H, hr. s), 7.93 (2H, hr. d, J=9.0Hz).

IR (KBr) ν: 1635, 1600, 1485, 1390, 1340, 1240, 1145, 885 cm⁻¹.

EXAMPLE 7

3,7-Bis[N-(5-succinimidoxycarbonylpentyl)-N-methylamino]phenazathionium chloride and 3-[N-(5-succinimidoxycarbonylpentyl)-N-methylamino]-7-[N-(5-carboxypentyl)-N-methylamino]phenazathionium chloride

Method A 3,7-Bis[N-(5-carboxypentyl)-N-methylamino]phenazathionium chloride (0.15 g) was dissolved in trifluoroacetic acid (10 ml) and the solution was concentrated to dryness. The trifluoroacetate thus obtained was dissolved in acetonitrile (30 ml) and DSC (0.92 g) and pyridine (0.85 ml) were added. The resulting mixture was stirred at room temperature for 15 hours. The reaction mixture was concentrated to dryness and the residue was dissolved by addition of dichloromethane. The solution was washed with saturated brine twice, dried over anhydrous sodium sulfate and concentrated. The residue was subjected to Sephadex ® LH-20 column chromatography and eluted with acetonitrile to obtain a bissuccinimido ester derivative (38 mg) as a first fraction and a monosuccinimido ester derivative (36 mg) as a second fraction.

Method B 3,7-Bis[N-(5-carboxypentyl)-N-methylamino]phenazathionium chloride (0.32 g) was dissolved in dimethylformamide (5 ml). N-Hydroxysuccinimide (0.42 g) and WSC (0.70 g) were added and the mixture was stirred for 3 hours. The reaction mixture was concentrated to dryness under reduced pressure and then extracted with dichloromethane. The dichloromethane layer was washed with saturated brine twice, dried over anhydrous sodium sulfate and concentrated. The residue was subjected to Sephadex ® LH-20 column chromatography and eluted with acetonitrile. The desired fractions were concentrated. The concentrate was dissolved in a small amount of dichloromethane and ethyl acetate was added to obtain a bissuccinimido ester derivative (83 mg) as purplish deep blue powder.

Bissuccinimido Ester

NMR (DMSO-$d_6$) δ (ppm): 1.40–1.55 (4H, m), 1.65–1.75 (8H, m), 2.71 (4H, t, J=7.0Hz), 2.82 (8H, s), 3.31 (6H, s), 3.75 (4H, br. t, J=7.0Hz), 7.51 (2H, br. s), 7.54 (2H, br. d, J=9.5Hz), 7.93 (2H, d, J=9.5Hz).

IR (KBr) ν: 1810, 1780, 1735, 1595, 1390, 1335, 1200, 1135, 1065, 880 cm$^{-1}$.

Monosuccinimido Ester

NMR (DMSO-$d_6$) δ (ppm): 1.35–1.65 (4H, m), 1.65–1.80 (8H, m), 2.24 (2H, t, J=7.0Hz), 2.71 (2H, t, J=7.0Hz), 2.82 (4H, s), 3.35 (6H, s), 3.74 (4H, br. t, J=7.0Hz), 7.50 (2H, s), 7.52 (2H, br. d, J=9.5Hz), 7.92 (2H, d, J=9.5Hz).

IR (KBr) ν: 1810, 1780, 1735, 1595, 1390, 1335, 1200, 1065, 880 cm$^{-1}$.

EXAMPLE 8

3-[N-(5-Succinimidoxycarbonylpentyl)-N-methylamino]-7-[N-[5-(1,3-dicarboxypropylcarbamoyl)pentyl]-N-methylamino]phenazathionium chloride A solution prepared from glutamic acid (27 mg), water (3 ml) and triethylamine (51 μl) was added to a solution of 3,7-bis[N-(5-succinimidoxycarbonylpentyl)-N-methylamino]phenazathionium chloride (72 mg) in acetonitrile (6 ml). After 5 minutes, 1N hydrochloric acid (0.35 ml) was added. The resulting mixture was subjected to Sephadex ®LH-20 column chromatography and eluted with acetonitrile to obtain the desired compound (16 mg).

NMR (DMSO-$d_6$) δ (ppm): 1.35–1.60 (4H, m), 1.60–1.80 (8H, 1.80–2.00 m), 2.15 (2H, t, J=6.0Hz), 2.27 (2H, t, J=7.0Hz), 2.71 (2H, t, J=7.0Hz), 2.82 (4H, s), 3.35 (6H, s), 3.72 (4H, br. s), 4.20 (1H, m), 7.40–7.55 (4H, m), 7.92 (1H, d, J=9.5Hz), 8.04 (1H, d, J=9.5Hz).

IR (KBr) ν: 1810, 1780, 1735, 1650, 1595, 1390, 1335, 1235, 1200, 1135, 1065, 880 cm$^{-1}$.

REFERENCE EXAMPLE 23

N-(3-Maleimidopropyl)-N-methylaniline

N-(3-Aminopropyl)-N-methylaniline [S. L. Shapiro et al., J. Am. Chem. Soc., 81, 3081 (1958)](8.3 g) was dissolved in dichloromethane (50 ml). Maleic anhydride (6 g) was added portionwise under ice-cooling and the mixture was stirred at room temperature for 1 hour. The solvent was distilled off and then acetic anhydride (20 ml) was added. The resulting mixture was allowed to stand at room temperature for 2 days. The reaction mixture was stirred at 60° C. for 2 hours and further at 100° C. for 2 hours. The mixture was concentrated under reduced pressure and the residue was extracted with ethyl acetate. The organic layer was neutralized with an aqueous sodium bicarbonate, washed with saturated brine and dried over anhydrous sodium sulfate. After concentration, the residue was subjected to column chromatography on silica gel and eluted with hexane/ethyl acetate (4:1). The desired compound thus obtained was recrystallized from the same solvent to obtain the compound as yellow needles (4.1 g).

m.p.: 87°–88° C.

NMR (CDCl$_3$) δ (ppm): 1.89 (2H, quintet, J=7.3Hz), 2.91 (3H, s), 3.33 (2H, t, J=7.3Hz), 3.57 (2H, t, J=7.3Hz), 6.68 (3H, m), 6.69 (2H, s), 7.21 (2H, m).

IR (KBr) ν: 1700, 1600, 1510, 1410, 1410, 1370, 1220, 830, 750, 690 cm$^{-1}$.

Elemental Analysis for $C_{14}H_{16}N_2O_2$, Calcd.: C, 68.83; H, 6.60; N, 11.47; Found : C, 68.95; H, 6.77; N, 11.49.

REFERENCE EXAMPLE 24

3-[N-(3-Maleimidopropyl)-N-methylamino]-7-[N-(3-ethoxycarbonylpropyl)-N-methylamino]phenazathionium chloride N-(3-Maleimidopropyl)-N-methylaniline (0.25 g) was dissolved in acetone (10 ml) and 1N hydrochloric acid (1 ml) and water (9ml) were added. Then 2-amino-5-[N-(3-ethoxycarbonylpropyl)-N-methylamino]phenylthiosulfonic acid (0.35 g) was added and further a solution of sodium dichromate 2 hydrate (0.2 g) in water (2 ml) was added dropwise with stirring. The resulting mixture was stirred at the same temperature for 30 minutes. Acetic acid (0.03 ml) was added and further stirred at room temperature for 30 minutes. Then catalytic amount of copper sulfate and manganese dioxide (0.25 g) were added. The mixture was stirred at room temperature for 30 minutes and further at 70° C. for 1 hour. After cooling, the reaction mixture was filtered. The residue was washed with ethanol and the washings were combined with the filtrate and the mixture was concentrated under reduced pressure. The residue was extracted with ethanol and insoluble materials were filtered off. The filtrate was concentrated. Then residue was subjected to column chromatography on silica gel and eluted with $CH_3CN$ followed by $CH_3CN/H_2O/1N$ HCl (40:5:1) to obtain the desired compound (0.31 g).

NMR ($CDCl_3$) δ (ppm): 1.28 (3H, t, J=7.2Hz), 1.78 (4H, m), 2.55 (2H, m), 3.39 (3H, s), 3.46 (3H, s), 3.60–3.95 (6H, m), 4.17 (2H, q, J=7.2Hz), 6.80 (2H, s), 7.15–8.00 (6H, m).

IR (KBr) ν: 1720, 1700, 1590, 1390, 1330, 1225, 1180, 1140, 880 cm$^{-1}$.

EXAMPLE 9

3-[N-(3-Maleimidopropyl)-N-methyamino]-7-[N-(3-carboxypropyl)-N-methylamino]phenazathionium chloride 3-[N-(3-Maleimidopropyl)-N-methylamino]-7-[N-(3-ethoxycarbonylpropyl)-N-methylamino]phenazathionium chloride (0.3 g) was dissolved in a mixture of acetonitrile (2 ml) and 1N hydrochloric acid (6 ml). The solution was left open for 2 days. The resulting precipitate having metallic luster was filtered off, washed with ether and dried to obtain the desired compound (0.25 g).

NMR (DMSO-$d_6$) δ (ppm): 1.90 (4H, m), 2.93 (2H, t, J=6.5Hz), 3.23 (3H, s), 3.35 (3H, s), 3.54 (2H, m), 7.01 (2H, s), 7.40–7.65 (4H, m), 7.85–8.00 (2H, m).

IR (KBr) ν: 1735, 1700, 1595, 1390, 1330 cm$^{-1}$.

EXAMPLE 10

3-[N-(3-Maleimidopropyl)-N-methylamino]-7-[N-[3-(1,3-dicarboxypropylcarbamoyl)propyl]-N-methylamino]phenazathionium chloride 3-[N-(3-Maleimidopropyl)-N-methylamino]-7-[N-(3-carboxypropyl)-N-methylamino]phenazathionium chloride (51 mg) was dissolved in dimethylformamide (5 ml) and dried over 4 Å molecular sieve. N-Hydroxysuccinimide (25 mg) and WSC (50 mg) were added thereto and the resulting mixture was allowed to react at room temperature for 23 hours. This reaction mixture was added to a solution prepared from L-glutamic acid (17.7 mg), dimethylformamide (5 ml), water (0.5 ml) and triethylamine (34 μl) under ice-cooling. The resulting mixture was stirred for 1 hour. The mixture was concentrated under reduced pressure. Then the residue was dissolved in water (5 ml) and 1N hydrochloric acid (0.24 ml) was added to the solution. The resulting solution was subjected to column chromatography on silica gel and eluted with $CH_3CN/H_2O$ (9:1) followed by $CH_3CN/H_2O/1N$ HCl (30:15:1). The desired fraction was concentrated. The residue was subjected to Sephadex ® LH-20 column chromatography and eluted with $CH_3CN/H_2O$ (10:1). The desired fractions was lyophilized to obtain the desired compound (26 mg).

NMR ($D_2O$) δ (ppm): 1.60–2.30 (6H, m), 2.45 (4H, m), 3.14 (6H, s), 3.35–3.65 (6H, m), 4.35 (1H, t), 6.80–7.50 (6H, m), 6.92 (2H, s).

IR (KBr) ν: 1730, 1700, 1640, 1595, 1390, 1330 cm$^{-1}$.

REFERENCE EXAMPLE 25

N-(3-Cyanopropyl)-N-methylaniline

To N-methylaniline (25 g) was added 4-chlorobutyronitrile (25 ml) and the mixture was stirred at 110° C. for 24 hours. After cooling, the mixture was neutralized with an aqueous sodium bicarbonate and extracted with ethyl acetate. The organic layer was washed with saturated brine, dried over anhydrous sodium sulfate and concentrated. The residue was subjected to distillation under reduced pressure to obtain the desired compound (21.5 g) as pale yellow oil.

b.p.: 118°–121° C./0.5 mmHg.

NMR ($CDCl_3$) δ (ppm): 1.96 (2H, quintet, J=7.0Hz), 2.40 (2H, t, J=7.0Hz), 2.96 (3H, s), 3.47 (2H, t, J=7.0Hz), 6.74 (3H, m), 7.25 (2H, m).

IR (neat) ν: 2950, 2875, 2825, 2250, 1600, 1505, 1370, 1190, 750, 690 cm$^{-1}$.

REFERENCE EXAMPLE 26

N-(4-Aminobutyl)-N-methylaniline

Lithium aluminium hydride (2 g) was added to dry ether (50 ml) in a stream of nitrogen, and a solution of N-(3-cyanopropyl)-N-methylaniline (9 g) in dry ether (10 ml) was added dropwise. The mixture was stirred for 1 hour and then heated under reflux for 2 hours. After decomposition of the excess reducing agent with ethyl acetate, the organic layer was washed with water, dried over anhydrous sodium sulfate and concentrated to obtain the desired compound (9.8 g) as colorless oil.

NMR ($CDCl_3$) δ (ppm): 1.54 (4H, m), 2.73 (2H, t, J=7.0Hz), 2.93 (3H, s), 3.33 (2H, t, J=7.0Hz), 6.70 (3H, m), 7.22 (2H, m).

REFERENCE EXAMPLE 27

N-(4-Maleimidobutyl)-N-methylaniline

N-(4-Aminobutyl)-N-methylaniline (7.2 g) was dissolved in dichloromethane (70 ml) and maleic anhydride (4 g) was added thereto. The mixture was stirred at room temperature for 2 hours. The solvent was distilled off and then acetic anhydride (10 ml) was added. The resulting mixture was stirred at 100° C. for 5 hours. After concentration, an aqueous sodium bicarbonate was added to the residue to neutralize it. The mixture was extracted with ethyl acetate. The organic layer was washed with saturated brine, dried over anhydrous sodium sulfate and concentrated under reduced pressure. The residue was subjected to column chromatography on silica gel and eluted with hexane/ethyl acetate (2:1) to obtain the desired compound (2.0 g) as yellow needles.

m.p.: 66°–67° C.

NMR ($CDCl_3$) δ (ppm): 1.60 (4H, m), 2.91 (3H, s), 3.33 (2H, t, J=6.8Hz), 3.54 (2H, t, J=6.8Hz), 6.68 (2H, s), 6.68 (3H, m), 7.22 (2H, m).

IR (KBr) ν : 1695, 1600, 1505, 1410, 1365, 750, 690 cm$^{-1}$.

Elemental Analysis for $C_{15}H_{18}N_2O_2$, Calcd.: C, 69.74; H, 7.02; N, 10.84; Found : C, 69 98; H, 7 20; N, 10.92.

REFERENCE EXAMPLE 28

N-(4-Ethoxycarbonylbutyl)-N-methyl-p-phenylenediamine

N-(4-Ethoxycarbonylbutyl)-N-methylaniline (2.35 g) obtained in Reference Example 2 was dissolved in 1N hydrochloric acid (30 ml) and to the solution was added dropwise a solution of sodium nitrite (0.76 g) in water (5 ml) at 0° to 4° C. The mixture was stirred at the same temperature for 30 minutes. To the resulting mixture was added 3N hydrochloric acid (15 ml) followed by zinc powder (2 g) at 20° to 27° C. The mixture was stirred at the same temperature for additional 1 hour. Sodium bicarbonate was added to the reaction mixture to neutralized it. The reaction mixture was extracted with ethyl acetate. The organic layer was washed with saturated brine, dried over anhydrous sodium sulfate and then concentrated. The concentrate was subjected to flush column chromatography on silica gel and eluted with hexane/ethyl acetate (1:1) to obtain the desired compound (1.7 g) as brown oil.

NMR (CDCl$_3$) δ (ppm): 1.25 (3H, t, J=7.2Hz), 1.61 (4H, m), 2.31 (2H, t, J=7.1 Hz), 2.81 (3H, s), 3.18 (2H, t, J=6.5Hz), 4.12 (2H, q, J=7.2Hz), 6.65 (4H, s).

REFERENCE EXAMPLE 29

2-Amino-5-[N-(4-ethoxycarbonylbutyl)-N-methylamino]phenylthiosulfonic acid

N-(4-Ethoxycarbonylbutyl)-N-methyl-p-phenylenediamine (1.7 g) was dissolved in 1N hydrochloric acid (13.6 ml) and to the solution was added a solution of aluminium sulfate 14–18 hydrate in water (10 ml). The mixture was ice-cooled. A solution of sodium thiosulfate 5 hydrate (2 g) in water (8 ml) was added thereto and further a solution of sodium dichromate 2 hydrate (0.798 g) in water (5 ml) was added dropwise. The resulting mixture was stirred for 30 minutes under ice-cooling. Then acetic acid (0.6 ml) was added and the mixture was further stirred at room temperature for 2 hours. The reaction mixture was concentrated to dryness. The concentrate was made alkaline with an aqueous sodium bicarbonate and insoluble materials were filtered off. The filtrate was adjusted to pH 4 with acetic acid, concentrated to about 50 ml and cooled. The resulting crystalline precipitate was filtered off, washed with cold water and dried to obtain the desired compound (2.1 g).

NMR (DMSO-d$_6$+D$_2$O) δ (ppm): 1.64 (3H, t, J=7.0Hz), 1.51 (4H, m), 2.30 (2H, m), 3.01 (3H, s), 3.39 (2H, m), 4.04 (2H, q, J=7.0Hz), 6.80–7.40 (3H, m).

IR (KBr) ν: 1720, 1620, 1250, 1180, 1110, 630 cm$^{-1}$.

REFERENCE EXAMPLE 30

3-[N-(4-Maleimidobutyl)-N-methylamino]-7-[N-(4-ethoxycarbonylbutyl)-N-methylamino]phenazathionium chloride N-(4-Maleimidobutyl)-N-methylaniline (0.26 g) obtained Reference Example 27 was dissolved in acetone (10 ml), and 1N hydrochloric acid (1 ml) and water (9 ml) were added thereto. The mixture was ice-cooled. To the mixture was added 2-amino-5-[N-(4-ethoxycarbonylbutyl)-N-methylamino]phenylthiosulfonic acid (0.4 g) followed by a solution of sodium dichromate 2 hydrate (0.2 g) in water (1 ml). The resulting mixture was stirred for 30 minutes. Acetic acid (0.03 ml) was added and the mixture was further stirred at room temperature for 1 hour. Then catalytic amount of copper sulfate and manganese dioxide (0.25 g) were added, and the resulting mixture was stirred at room temperature for 30 minutes and further at 70° C. for 1 hour. After cooling, the reaction mixture was filtered and the residue was washed with methanol and water. The filtrate was concentrated to dryness and mixed with saturated saline and chloroform with shaking. The organic layer was dried over anhydrous sodium sulfate and concentrated. The residue was subjected to column chromatography on silica gel and eluted with CH$_3$CN followed by CH$_3$CN/H$_2$O/1N HCl (40:5:1). The desired fraction was concentrated. Acetonitrile was added to the concentrate and insoluble materials were filtered off. The filtrate was concentrated to dryness to obtain the desired compound (0.289 g).

NMR (CDCl$_3$) δ (ppm): 1.26 (3H, t, J=7.0Hz), 1.77 (8H, m), 2.41 (2H, t, J=5.7Hz), 3.40 (3H, s), 3.61 (2H, t, J=6.0Hz), 3.77 (4H, m), 4.13 (2H, q, J=7.0Hz), 6.78 (2H, s), 7.65–7.96 (6H, m).

IR (KBr) ν: 1720, 1700, 1595, 1390, 1330, 1140, 880 cm$^{-1}$.

EXAMPLE 11

3-[N-(4-Maleimidobutyl)-N-methylamino]-7-[N-(4-carboxybutyl)-N-methylamino]phenazathionium chloride 3-[N-(4-Maleimidobutyl)-N-methylamino]-7-[N-(4-ethoxycarbonyl)butyl-N-methylamino]phenazathionium chloride (0.287 g) was dissolved by addition of acetonitrile (2 ml) and 1N hydrochloric acid (6 ml). The solution was left open for 44 hours. The resulting precipitate having metallic luster was filtered off, washed with ether and dried to obtain the desired compound (0.246 g).

NMR (DMSO-d$_6$) δ (ppm): 1.61 (8H, m), 2.30 (2H, t, J=6.0Hz), 3.76 (4H, m), 7.03 (2H, s), 7.52 (4H, br. s), 7.85–8.00 (2H, m).

IR (KBr) ν: 1740, 1700, 1390, 1330 cm$^{-1}$.

EXAMPLE 12

3-[N-(4-Maleimidobutyl)-N-methylamino]-7-dimethylaminophenazathionium chloride

N-(4-Maleimidobutyl)-N-methylaniline (0.26 g) obtained in Reference Example 27 was dissolved in acetone (10 ml), and 1N hydrochloric acid (1 ml) and water (10 ml) were added thereto. The mixture was ice-cooled. To the mixture was added 2-amino-5-dimethylaminophenylthiosulfonic acid (0.25 g). Then a solution of sodium dichromate 2 hydrate (0.2 g) in water (2 ml) was added dropwise. The resulting mixture was stirred at the same temperature for 30 minutes. Then acetic acid (0.03 ml) was added thereto and the mixture was further stirred at room temperature for 1 hour. Acetone was distilled off under reduced pressure. Precipitated insoluble materials having metallic luster were filtered and washed with water. The materials were suspended in 50% acetone-water (30 ml), and catalytic amount of copper sulfate and manganese dioxide (0.25 g) were added to the suspension. The mixture was stirred at room temperature for 1 hour and further at 70° C. for 1 hour. After cooling, the reaction mixture was filtered. The residue was washed successively with acetone, water and ethanol. The filtrate was concentrated to dryness. Then the residue was subjected to column chromatography on silica gel and eluted with CH$_3$CN followed by CH$_3$CN/H$_2$O/1N HCl (40:5:1). The desired fraction was concentrated. Chloroform (50 ml) and ethanol (4 ml) were added to the residue. Insoluble materials were filtered off and then the filtrate was concentrated to dryness to obtain the desired compound (0.42 g).

NMR (DMSO-d$_6$+D$_2$O) δ (ppm): 1.60 (4H, m), 3.31 (3H, s), 3.36 (6H, s), 3.47 (2H, m), 3.72 (2H, m), 7.00 (2H, s), 7.40–7.60 (4H, m), 7.85–7.96 (2H, m).

IR (KBr) ν: 1700, 1590, 1390, 1350, 1330 cm$^{-1}$.

EXAMPLE 13

Coupling of succinimidomethylene blue derivatives to BSA and denatured BSA

Bovine serum albumin (Miles Inc., Kankakee, Ill., USA) (50 mg) was dissolved in 25mM phosphate buffer (pH 7, 25 ml) containing 0.5% sodium lauryl sulfate and 0.25% β-mercaptoethanol. The solution was heated at 90° C. for 10 minutes. The reaction mixture was cooled and then subjected to Sephadex ® G-50 column gel filtration, and eluted with 25 mM phosphate buffer to separate the denatured protein from the reducing agent.

All buffers used hereinafter are 0.1M phosphate buffers (pH 7) unless otherwise stated.

The succinimidomethylene blue derivatives 1, 2, 3, 4, 5, 6, 7 and 8 (each 2 mg) were dissolved in the buffer (1 ml). The buffer (0.5 ml) containing BSA (1 mg) was added to each solution (0.5 ml) and the mixture was incubated at 6° C. overnight. The buffer (0.75 ml) containing the denatured BSA (0.5 mg) was added to each solution (0.25 ml) and the mixture was incubated at 6° C. overnight. Lysine (2 mg) was added to a solution of the succinimidomethylene blue derivative 1 which had been incubated overnight. Each solution was subjected to gel filtration using Sephadex ® G-50 column and the unreacted methylene blue derivative was removed.

The concentration of the protein in each conjugate the solution was determined by dye-binding assat (Bi-orad Laboratories, Richmond, Calif., U.S.A.). The amount of the coupled methylene blue derivative was estimated from absorbance at 662 nm.

Table 1 shows the number of the methylene blue derivatives incorporated into BSA and into denatured BSA (MB/BSA), and their relative chemiluminescence activities.

The chemical structures of the methylene blue derivatives are as follows:

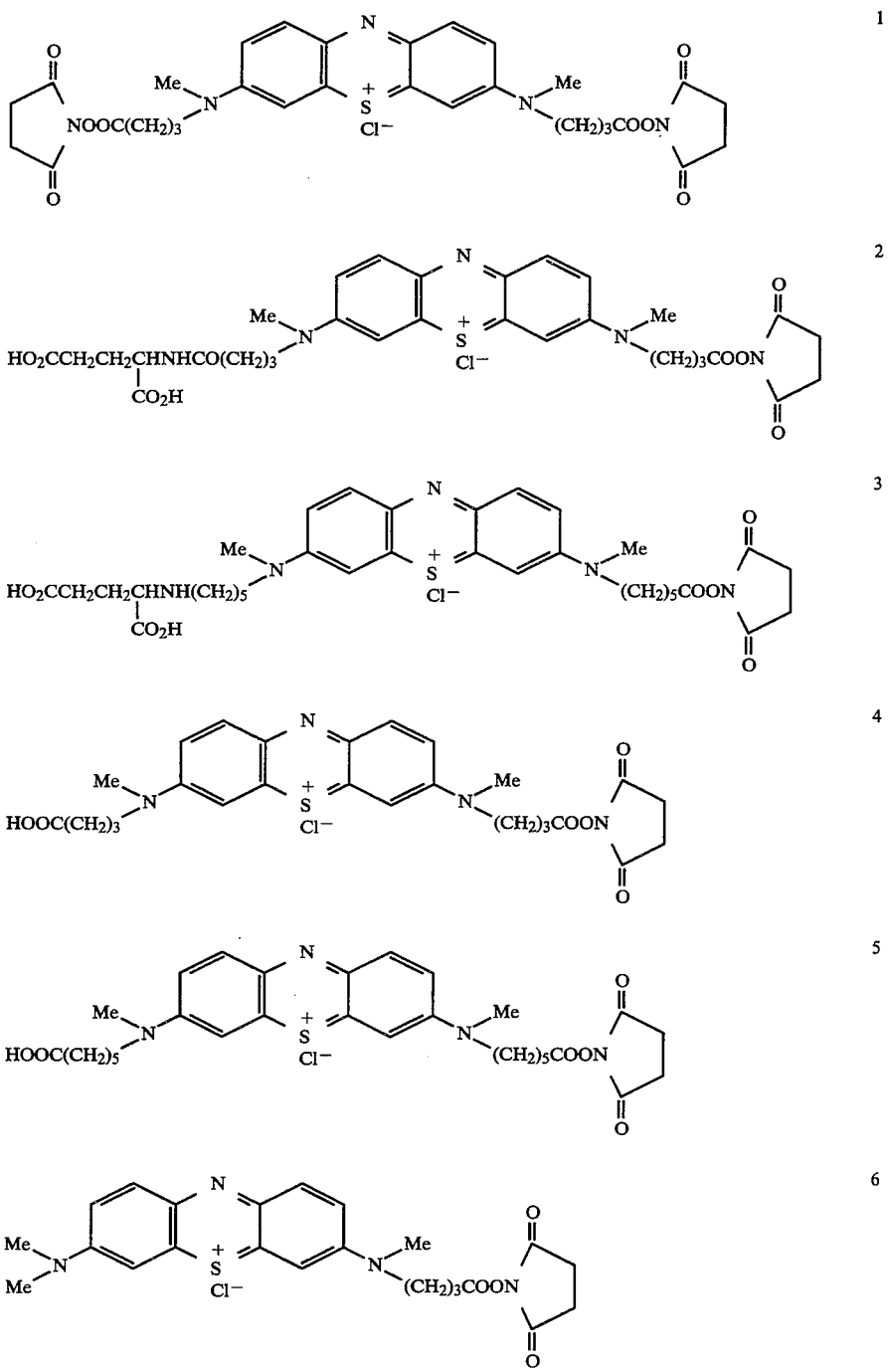

-continued

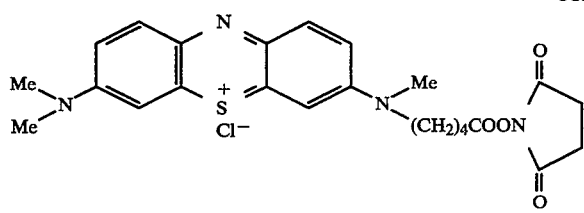

7

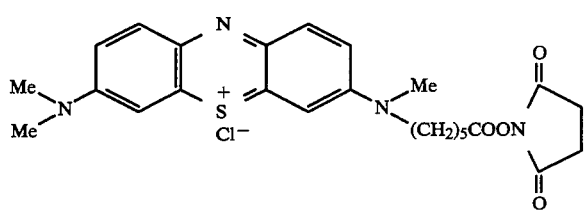

8

TABLE 1

| Deriva-tive No. | BSA | | Denatured BSA | |
|---|---|---|---|---|
| | MB/BSA | Relative Chemi-luminescence | MB/BSA | Relative Chemi-luminescence |
| 1 | 36 | 0.16 | 13.7 | 1.07 |
| 2 | 9.77 | 0.08 | 6.7 | 0.72 |
| 3 | 27 | 0.12 | 8.0 | 0.71 |
| 4 | 22 | 0.23 | 7.7 | 2.01 |
| 5 | 32 | 0.25 | 9.2 | 1.05 |
| 6 | * | 0.11 | 8.1 | 1.43 |
| 7 | * | 0.20 | 9.0 | 0.75 |
| 8 | * | 0.55 | 8.0 | 2.70 |

*formation of precipitate

EXAMPLE 14

Coupling of succinimidomethylene blue derivatives to IgG

The succinimidomethylene blue derivatives 2, 4, 6 and 8 (each 2 mg) were dissolved in the buffer (1 ml). Each solution was mixed with the buffer (0.5 ml) containing 0.5 mg of IgG (anti-alpha fetoprotein antibody A4-4, manufactured by Wako Pure Chemical Industries, Ltd., Osaka, Japan) so that the concentration of the derivative became 15, 50 or 200-fold molar ratio relative to IgG and the mixture was incubated at 6° C. overnight. Each solution was subjected to Sephadex ® G-50 gel filtration, and the unreacted methylene blue derivative was removed. The concentration of IgG and the methylene blue derivative (MB) was determined according to the method as described above. The antibody binding activity was determined by a competitive reaction between IgG-methylene blue derivative conjugate and IgG-HRP conjugate in ELISA of alpha fetoprotein.

The results are shown in Table 2.

TABLE 2

| Derivative No. (Molar Ratio) | MB/IgG binding ratio | Relative Chemiluminescence Activity | IgG Binding Activity (%) |
|---|---|---|---|
| 2 (15X) | 0.64 | 1.7 | 100 |
| 2 (50X) | 2.0 | 5.9 | ND |
| 2 (200X) | 4.3 | 19.4 | 16 |
| 4 (15X) | 1.6 | 4.9 | 100 |
| 4 (50X) | 5.3 | 16.4 | 100 |
| 4 (200X) | part precipitated | 19.4 | 20 |
| 6 (15X) | 2.1 | 4.8 | 100 |
| 6 (50X) | precipitate | 6.3 | 100 |
| 6 (200X) | precipitate | 9.3 | 15 |

TABLE 2-continued

| Derivative No. (Molar Ratio) | MB/IgG binding ratio | Relative Chemiluminescence Activity | IgG Binding Activity (%) |
|---|---|---|---|
| 8 (15X) | 3.1 | 3.0 | 100 |
| 8 (50X) | precipitate | 4.8 | 15 |
| 8 (200X) | precipitate | 1.6 | 13 |

ND: not determined

EXAMPLE 15

ELISA Using IgG-methylene Blue Derivative Conjugate

A 10% solution of latex of 3.2 µm in average diameter (Sigma Chemical Co., St. Louis, Mo. U.S.A.) (0.5 ml) was washed with water (5 ml) twice to prepare the solid phase. The latex thus obtained was washed with 0.1M carbonate buffer (pH 9.5, 5 ml) and then suspended in the same buffer (5 ml) again. The suspension was incubated at 56° C. for 20 minutes and then anti-alpha fetoprotein antibody (A2–95, manufactured by Wako Pure Chemical Industries, Ltd., Osaka, Japan) (1 mg) was added thereto. The resulting mixture was incubated for 40 minutes at 56° C. and then further for 2 hours at room temperature. The mixture was washed with 0.1M phosphate buffer (pH 6, 5 ml) containing 0.2% Tween-20 followed by phosphate buffered saline (5 ml, 50mM sodium phosphate, 0.8% sodium chloride, pH 7) containing 25% Block Ace (Snow Brand Products, Sapporo, Japan). The mixture was stored in phosphate buffered saline containing 25% Block Ace, 0.5% bovine serum albumin and 0.02% merthiolate.

In ELISA procedure, the 2% latex solution (50 µl) prepared above was mixed with IgG-methylene blue derivative conjugate (5 µl) obtained by incubating succinimidomethylene blue derivative 4 of 50-fold molar ratio with respect to IgG and phosphate buffered saline (250 µl) containing 10% Block Ace. Various concentrations of alpha fetoprotein was added thereto, and the resulting mixture was incubated at 37° C. for 30 minutes. Each of the mixtures was washed with phosphate buffered saline containing 0.1% Tween-20 four times followed by phosphate buffered saline. To each of the resulting mixtures was added 0.1M sodium hydroxide (0.4 ml) containing 1 mM luminol. Then the suspension was transferred to a plastic tube for the measurement by an Optically Pumped Chemiluminescence (OPC) method as described in (Japanese Patent Application No. 2-249879 corresponding to U.S. patent application Ser. No. 07/757,958 and European Application No. 91115648.7). The results are shown in FIG. 1. In FIG. 1, the ordinate axis indicates photons counted per minute (CPM) and the abscissa axis indicates the amount of alpha fetoprotein. From the results, the chemiluminescent output linearly increases in accordance with the amount of alpha fetoprotein.

EXAMPLE 16

ELISA Using Fab'-BSA-methylene Blue Derivative Conjugate

Figure 2:
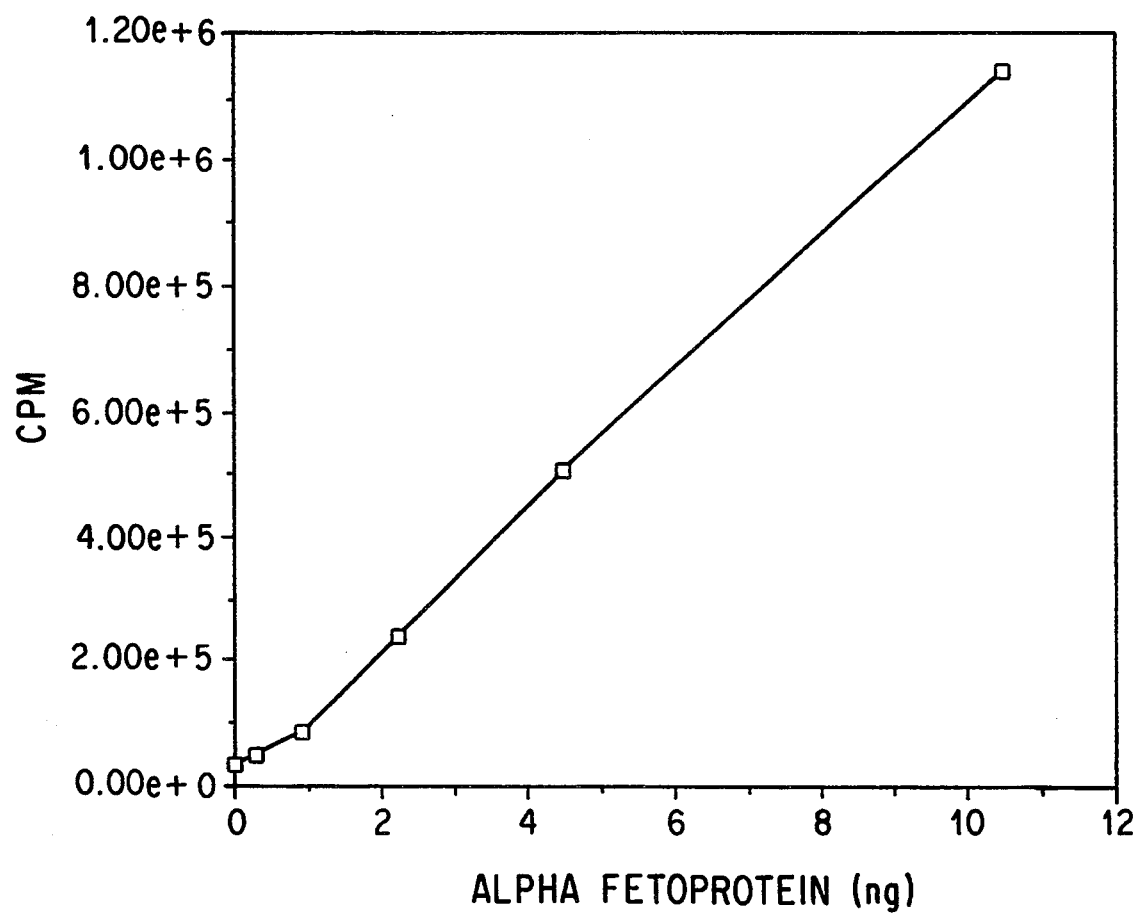
FIG. 2 illustrates the result of alpha fetoprotein assay obtained in Example 16 described hereinafter.

In this example, antibody fragment Fab'-methylene blue derivative conjugate was prepared by using bovine serum albumin as a carrier protein. F(ab')$_2$ (1 mg) prepared from anti- alpha fetoprotein antibody was reduced by incubating it in 1 ml of 0.1 M phosphate buffer (pH 6.8) containing 20mM dithiothreitol. The excess dithiothreitol was removed by gel filtration in the same buffer. The protein thus obtained was reacted with N,N'-bis(3-maleimidopropyl)-2-hydroxy-1,3-propanediamine (2 mg) at 37° C. for 30 minutes. The excess reagent was removed by gel filtration. According to the above-described method, bovine serum albumin (1 mg) was denatured, reacted with succinimidomethylene blue derivative 4 and then reduced with dithiothreitol. The protein was recovered from the gel filtration and mixed with the Fab' prepared above. The resulting mixture was incubated at 6° C. overnight. According to the same manner as that described in Example 15, the Fab'-BSA-methylene blue derivative conjugate thus prepared was used for the assay of alphaαfetoprotein. The results are shown in FIG. 2. In FIG. 2, the ordinate axis indicates CPM and the abscissa axis indicates the amount of alpha fetoprotein. As is apparent from the results, the chemiluminescent output linearly increases in accordance with the amount of alpha fetoprotein.

What is claimed is:

1. A phenothiazine derivative of the formula (I):

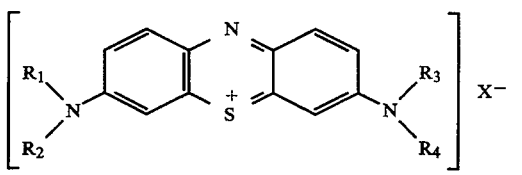

(I)

wherein R$_1$, R$_2$, R$_3$ and R$_4$ are the same or different and are respectively a C$_{1-6}$ alkyl group, at least one of which has as a substituent a group which can react with amino group, thiol group or carboxyl group, and X' is a counter ion of the phenazathionium.

2. A phenothiazine derivative according to claim 1, wherein the substituent is carboxyl group, halogenocarbonyl group, azidocarbonyl group, cyanocarbonyl group, an alkoxycarbonyloxycarbonyl group, a substituted phenoxycarbonyl group, 1-imidazolyl-carbonyl group, 1-benzotriazolyloxycarbonyl group, 5-norbornene-2,3-dicarboximidoxycarbonyl group, succinimidoxycarbonyl group, maleimidoxycarbonyl group, aspartic acid residue, glutamic acid residue, maleimido group, or an aminoalkylcarbamoyl group.

3. A phenothiazine derivative according to claim 2, wherein the substituent is carboxyl group, chlorocarbonyl group, azidocarbonyl group, cyanocarbonyl group, ethoxycarbonyloxycarbonyl group, isobutoxycarbonyloxycarbonyl group, p-nitrophenoxycarbonyl group, 2,4-dinitrophenoxycarbonyl group, pentachlorophenoxycarbonyl group, 2,4,5-trichlorophenoxycarbonyl group, pentafluorophenoxycarbonyl group, 1-imidazolyl-carbonyl group, 1-benzotriazolyloxycarbonyl group, 5-norbornene-2,3-dicarboximideoxycarbonyl group, succinimidoxycarbonyl group, maleimidoxycarbonyl group, aspattic acid residue, glutamic acid residue, maleimido group, aminoethylcarbamoyl group, or aminodecylcarbamoyl group.

4. A phenothiazine derivative according to claim 1, wherein the group X is the counter ion formed by a halogen atom, hydroxyl, perchloric acid, sulfuric acid, nitric acid, trifluoroacetic acid or hydrofluoroboric acid.

5. A phenothiazine derivative according to claim 1, which is hydrophilic.

6. A phenothiazine derivative according to claim 1 which is
  3-[N-methyl-N-(4-succinimidoxycarbonylbutyl-)amino]-7-dimethylaminophenazathionium chloride,
  3-[N-methyl-N-(5-succinimidoxycarbonylpentyl-)amino]-7-dimethylaminophenazathionium chloride,
  3-[N-methyl-N-(3-succinimidoxycarbonylpropyl-)amino]-7-dimethylaminophenazathionium chloride,
  3-[N-methyl-N-(3-succinimidoxycarbonylpropyl-)amino]-7-[N-(3-ethoxycarbonylpropyl)-N-methylamino]phenazathionium chloride,
  3,7-bis[N-methyl-N-(3-succinimidoxycarbonylpropyl)amino]phenazathionium chloride,
  3-[N-methyl-N-(3-succinimidoxycarbonylpropyl-)amino]-7-[N-(3-carboxypropyl)-N-methylamino]-phenazathionium chloride,
  3-[N-methyl-N-(3-succinimidoxycarbonylpropyl-)amino]-7-[N-[3-(1,3-dicarboxypropylcarbamoyl)-propyl]-N-methylamino]phenazathionium chloride,
  3,7-bis[N-methyl-N-(5-succinimidoxycarbonylpentyl)amino]phenazathionium chloride,
  3-[N-methyl-N-(5-succinimidoxycarbonylpentyl-)amino]-7-[N-(5-carboxypentyl)-N-methylamino]-phenazathionium chloride,
  3-[N-methyl-N-(5-succinimidoxycarbonylpentyl-)amino]-7-[N-[5-(1,3-dicarboxypropylcarbamoyl)-pentyl]-N-methyamino]phenazathiomium chloride,
  3-[N-(3-maleimidopropyl)-N-methylamino]-7-[N-(3-carboxypropyl]-N-methylamino]phenazathionium chloride,
  3-[N-(3-maleimidopropyl)-N-methylamino]-7-[N-[3-(1,3-dicarboxypropylcarbamoyl)propyl]-N-methylamino]phenazathionium chloride,
  3-[N-(4-maleimidobutyl)-N-methylamino]-7-[N-(4-carboxybutyl)-N-methylamino]phenazathionium chloride, or
  3-[N-(4-maleimidobutyl)-N-methylamino]-7-dimethylaminophenazathionium chloride.

7. A phenothiazine derivative of the formula (II):

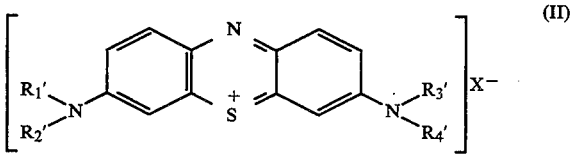

(II)

wherein at least one of $R_1'$, $R_2'$, $R_3'$ and $R_4'$ is a group of the formula: —(CH$_2$)m—CO—Y, the others are C$_{1-6}$ alkyl group, Y is a lower alkoxy group having 1 to 4 carbon atoms, an aralkyloxy group or a 1-phenoxy-ethoxy group, m is an integer of 1 to 6 and X− is a counter ion of the phenazathionium.

8. A phenothiazine derivative according to claim 7, wherein the group Y is methoxy, ethoxy, propoxy, secbutoxy, tert-butoxy, benzyloxy, p-nitrogenzyloxy, p-methylthiobnzyloxy, diphenylmethyloxy, 4-pyridyl-methoxy, or 1-phenoxy-ethoxy group.

9. A phenothiazine derivative according to claim 7, wherein the group X is the counter ion formed by a halogen atom, hydroxyl, perchloric acid, sulfuric acid, nitric acid, trifluoroacetic acid or hydrofluoroboric acid.

10. A phenothiazine derivative according to claim 7 which is
   3-[N-(4-ethoxycarbonylbutyl)-N-methylamino]-7-dimethylaminophenazathionium chloride,
   3-[N-(5-ethoxycarbonylpentyl)-N-methylamino]-7-dimethylaminophenazathionium chloride,
   3-[N-(3-tert-butoxycarbonylpropyl)-N-methylamino]-7-dimethylaminophenazathionium chloride,
   3-[N-(3-tert-butoxycarbonylpropyl)-N-methylamino]-7-[N-(3-ethoxycarbonylpropyl)-N-methylamino]phenazathionium chloride,
   3,7-bis]N-(3-tert-butoxycarbonylpropyl)-N-methylamino]phenazathionium chloride, or
   3,7-bis]N-(5-ethoxycarbonylpentyl)-N-methylamino]phenazathionium chloride.

\* \* \* \* \*

UNITED STATES PATENT AND TRADEMARK OFFICE
CERTIFICATE OF CORRECTION

PATENT NO. : 5,344,928
DATED : September 6, 1994
INVENTOR(S) : MASUYA et al.

It is certified that error appears in the above-indentified patent and that said Letters Patent is hereby corrected as shown below:

Column 35, line 52, Claim 1, contains a typographical error wherein "X'" should read --$\overline{X}$--;

Column 36, line 11, claim 4, "X" should read --$\overline{X}$--;

Column 37, line 9, claim 8, "p-nitrogenzyloxy" should read --p-nitrobenzyloxy--;

Column 37, line 10, claim 8, "p-methylthiobnzyloxy" should read --p-methylthiolbenzyloxy--;

Column 37, line 14, claim 9, "X" should read --$\overline{X}$--; and

Column 38, lines 13 and 15, "bis]" should read --bis[--.

Signed and Sealed this

Thirtieth Day of May, 1995

Attest:

BRUCE LEHMAN

*Attesting Officer*  *Commissioner of Patents and Trademarks*